United States Patent [19]
Landrau et al.

[11] Patent Number: 5,919,478
[45] Date of Patent: *Jul. 6, 1999

[54] INCORPORATING POLY-N-VINYL AMIDE IN A TRANSDERMAL SYSTEM

[75] Inventors: Felix A. Landrau, San Jose; Diane E. Nedberge, Los Altos; Linda Mary Hearney, Saratoga, all of Calif.

[73] Assignee: ALZA Corporation, Palo Alto, Calif.

[*] Notice: This patent issued on a continued prosecution application filed under 37 CFR 1.53(d), and is subject to the twenty year patent term provisions of 35 U.S.C. 154(a)(2).

[21] Appl. No.: 08/564,058

[22] PCT Filed: Jun. 24, 1994

[86] PCT No.: PCT/US94/07267

§ 371 Date: Dec. 14, 1995

§ 102(e) Date: Dec. 14, 1995

[87] PCT Pub. No.: WO95/01167

PCT Pub. Date: Jan. 12, 1995

Related U.S. Application Data

[63] Continuation-in-part of application No. 08/082,624, Jun. 25, 1993, abandoned.

[51] Int. Cl.$^6$ ............................................. A61F 13/00
[52] U.S. Cl. ................... 424/449; 424/448; 514/946
[58] Field of Search .................... 424/448, 449; 514/946

[56] References Cited

U.S. PATENT DOCUMENTS

| | | | |
|---|---|---|---|
| 3,472,931 | 10/1969 | Stoughton | 424/180 |
| 3,527,864 | 9/1970 | MacMillan et al. | 424/177 |
| 3,598,122 | 8/1971 | Zaffaroni | 128/268 |
| 3,598,123 | 8/1971 | Zaffaroni | 128/268 |
| 3,731,683 | 5/1973 | Zaffaroni | 128/268 |
| 3,797,494 | 3/1974 | Zaffaroni | 128/268 |
| 3,896,238 | 7/1975 | Smith | 424/358 |
| 3,903,256 | 9/1975 | MacMillan et al. | 424/59 |
| 3,952,099 | 4/1976 | Smith | 424/227 |
| 4,031,894 | 6/1977 | Urquhart et al. | 128/268 |
| 4,046,886 | 9/1977 | Smith | 424/227 |
| 4,130,643 | 12/1978 | Smith | 424/238 |
| 4,130,667 | 12/1978 | Smith | 424/361 |
| 4,144,317 | 3/1979 | Higuchi et al. | 424/21 |
| 4,201,211 | 5/1980 | Chandrasekaran et al. | 128/268 |
| 4,286,592 | 9/1981 | Chandrasekaran | 128/260 |
| 4,291,015 | 9/1981 | Keith . | |
| 4,299,826 | 11/1981 | Luedders | 424/181 |
| 4,314,557 | 2/1982 | Chandrasekaran | 128/260 |
| 4,335,115 | 6/1982 | Thompson et al. | 424/181 |

(List continued on next page.)

FOREIGN PATENT DOCUMENTS

| | | |
|---|---|---|
| 0 416 842 | 3/1991 | European Pat. Off. ........ A61L 15/04 |
| 0 664 119 A2 | 7/1995 | European Pat. Off. . |
| 1001949 | 7/1962 | Germany ......................... A61K 3/00 |
| 4234314 | 8/1992 | Japan . |
| 93/07870 | 4/1993 | WIPO ............................ A61K 31/40 |
| 93/08795 | 5/1993 | WIPO . |
| 95/18603 | 7/1995 | WIPO . |

OTHER PUBLICATIONS

Idson, Bernard, Percutaneous Absorption, J. of Phar. Sci., vol. 64, No. 6, Jun. 1975 pp. 901–924.

*Primary Examiner*—D. Gabrielle Brouillette
*Attorney, Agent, or Firm*—Michael J. Rafa; Steve F. Stone

[57] ABSTRACT

The present invention comprises a composition comprising a matrix adapted to be placed in drug-and permeation-enhancing mixture-transmitting relation to a selected skin or other body site. The matrix contains sufficient amounts of drug, permeation enhancer(s) and poly-N-vinylamide to continuously administer to the site, the drug, in a therapeutically effective amount, and the permeation-enhancing mixture, in an amount effective to enhance the permeation of the skin to the drug. The device shows increased transdermal flux, as compared to the transdermal flux of the drug from a device containing no poly-N-vinyl amide. Incorporating poly-N-vinyl amide into the transdermal system also improves the adhesion and stability of the system.

9 Claims, 16 Drawing Sheets

U.S. PATENT DOCUMENTS

| | | | |
|---|---|---|---|
| 4,343,798 | 8/1982 | Fawzi | 424/240 |
| 4,379,454 | 4/1983 | Campbell et al. | 604/897 |
| 4,405,616 | 9/1983 | Rajadhyaksha | 424/244 |
| 4,435,180 | 3/1984 | Leeper | 604/896 |
| 4,438,139 | 3/1984 | Keith . | |
| 4,466,953 | 8/1984 | Keith et al. | 424/28 |
| 4,470,962 | 9/1984 | Keith et al. | 424/28 |
| 4,472,372 | 9/1984 | Keith et al. | 424/19 |
| 4,492,685 | 1/1985 | Keith et al. | 424/28 |
| 4,559,222 | 12/1985 | Enscore et al. | 424/28 |
| 4,573,995 | 3/1986 | Cheng et al. | 604/896 |
| 4,579,731 | 4/1986 | Fox, Jr. et al. | 424/28 |
| 4,588,580 | 5/1986 | Gale et al. | 424/21 |
| 4,626,539 | 12/1986 | Aungst et al. | 514/282 |
| 4,645,502 | 2/1987 | Gale et al. | 604/896 |
| 4,668,232 | 5/1987 | Cordes . | |
| 4,695,465 | 9/1987 | Kigasawa . | |
| 4,704,282 | 11/1987 | Campbell et al. | 424/449 |
| 4,746,515 | 5/1988 | Cheng et al. | 424/449 |
| 4,781,926 | 11/1988 | Hyon . | |
| 4,788,062 | 11/1988 | Gale et al. | 424/449 |
| 4,816,258 | 3/1989 | Nedberge et al. | 424/448 |
| 4,849,226 | 7/1989 | Gale | 424/448 |
| 4,863,970 | 9/1989 | Patel et al. | 514/784 |
| 4,908,027 | 3/1990 | Enscore et al. | 604/890 |
| 4,943,435 | 7/1990 | Baker et al. | 424/448 |
| 4,973,708 | 11/1990 | Digenis et al. | 548/544 |
| 4,996,199 | 2/1991 | Minaskanian et al. | 514/167 |
| 5,004,610 | 4/1991 | Osborne et al. | 424/448 |
| 5,032,402 | 7/1991 | Digenis et al. | 424/448 |
| 5,095,054 | 3/1992 | Lay et al. | 524/47 |
| 5,154,922 | 10/1992 | Govil et al. | 424/448 |
| 5,176,916 | 1/1993 | Yamanaka et al. | 424/448 |
| 5,230,898 | 7/1993 | Horstmann et al. | 424/449 |
| 5,232,703 | 8/1993 | Blank | 424/449 |
| 5,252,588 | 10/1993 | Azuma et al. | 514/317 |
| 5,411,740 | 5/1995 | Lee | 424/448 |
| 5,413,776 | 5/1995 | Suzuki et al. | 424/448 |
| 5,556,635 | 9/1996 | Istin et al. | 424/448 |
| 5,676,968 | 10/1997 | Lipp et al. | 424/448 |

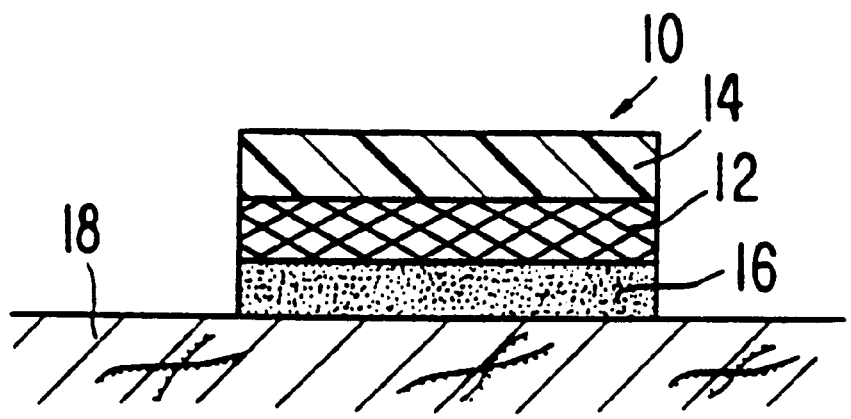
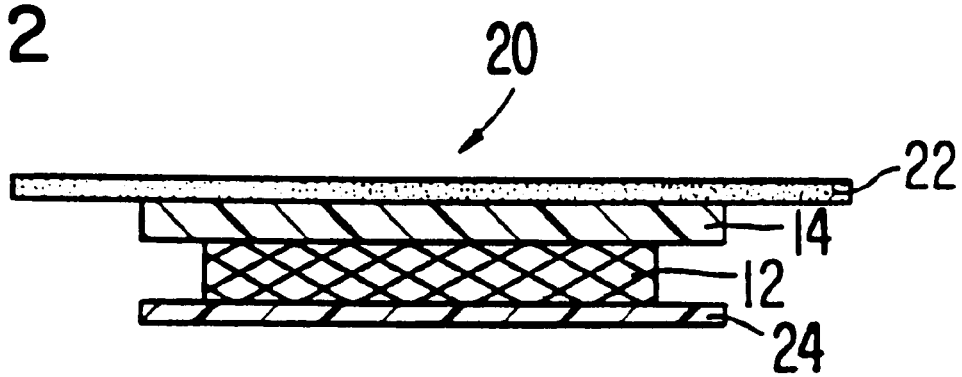
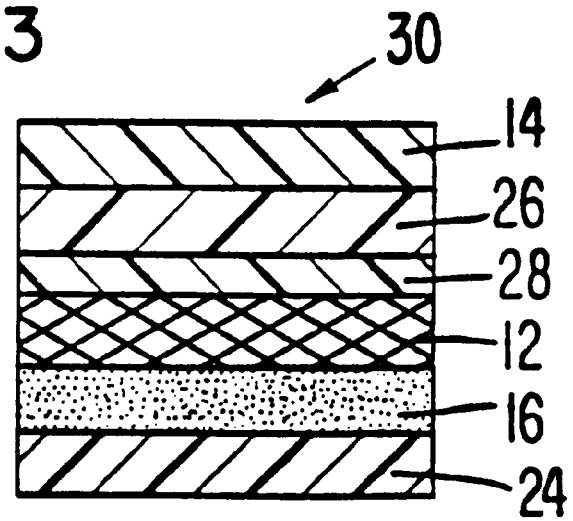

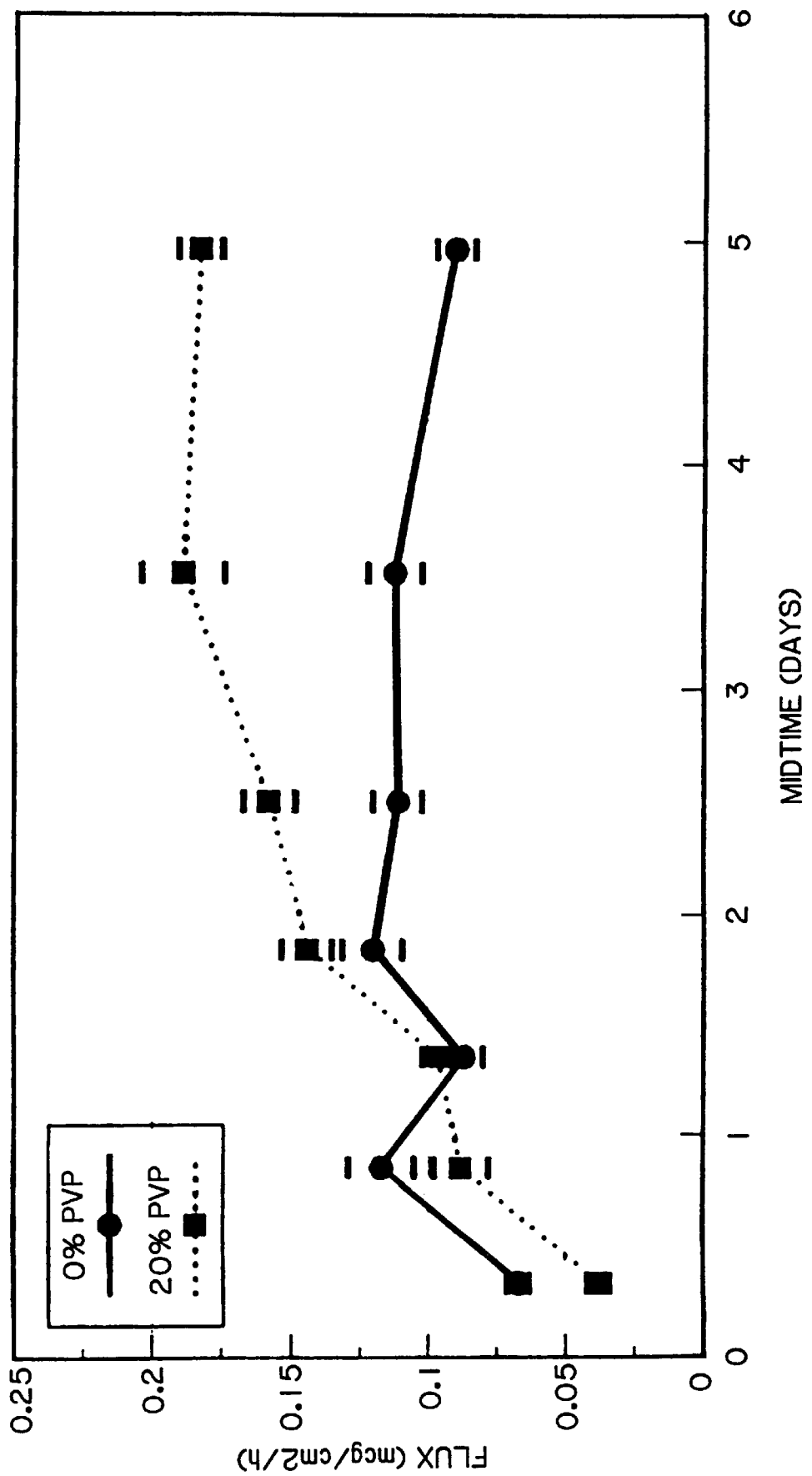

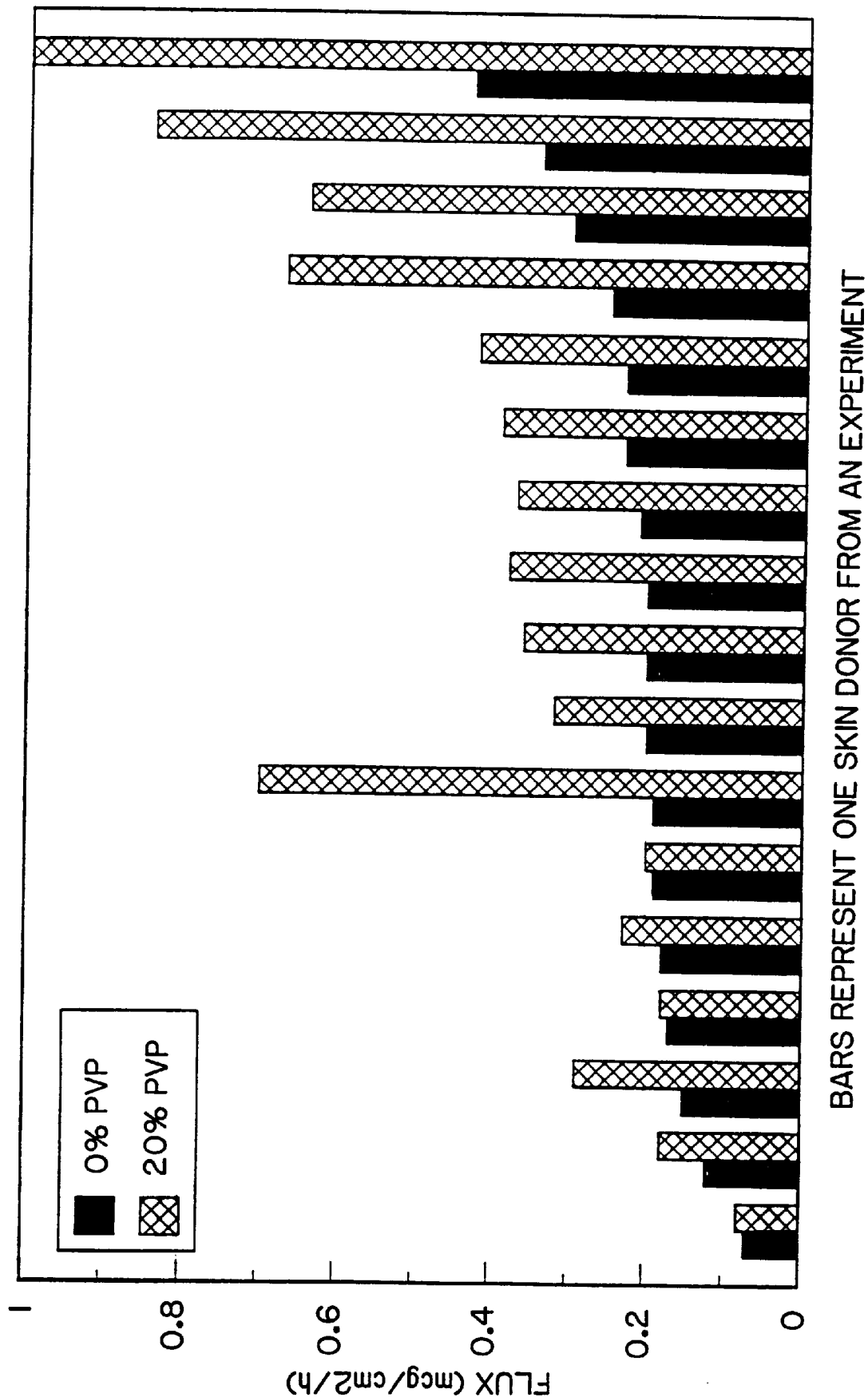

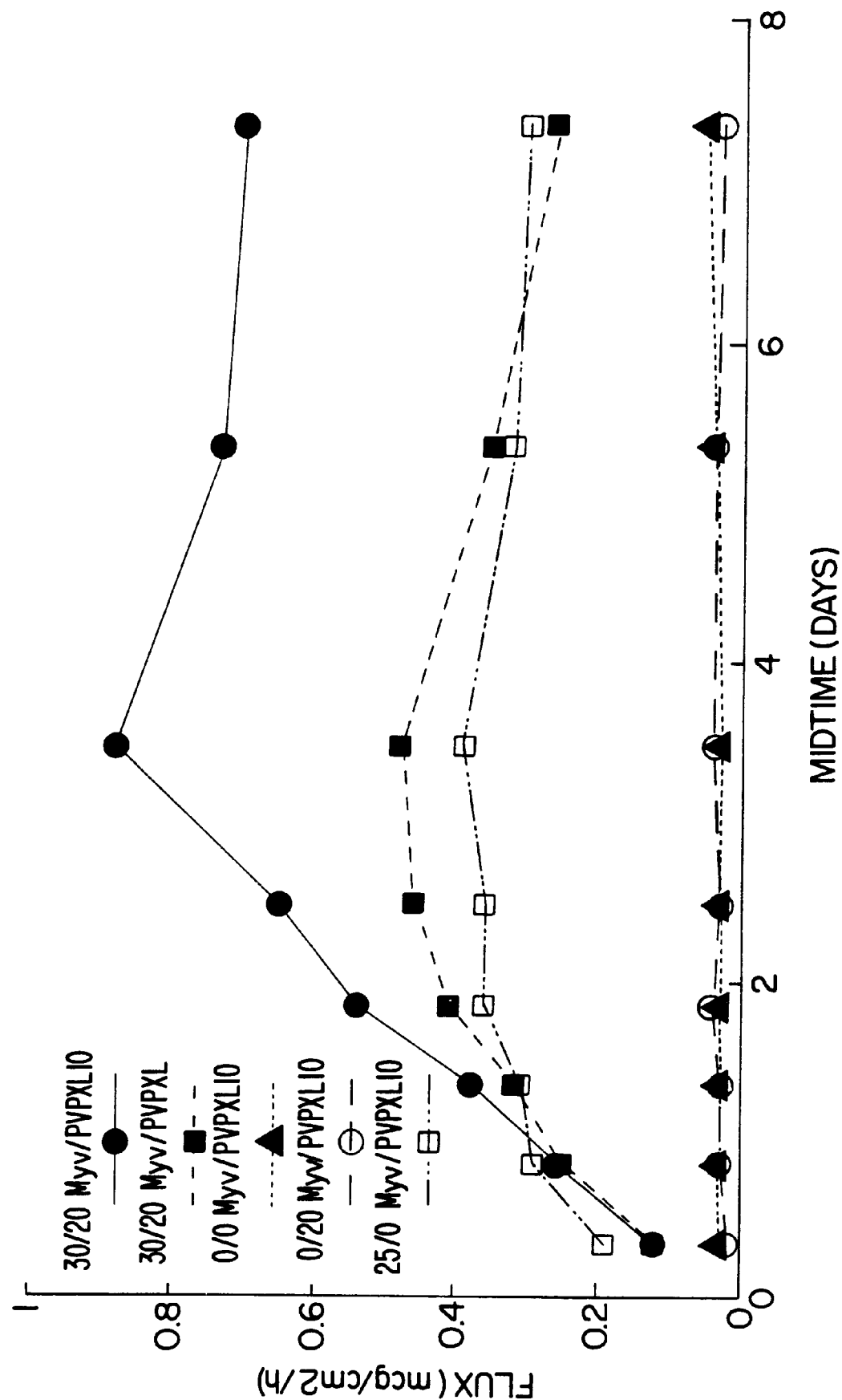

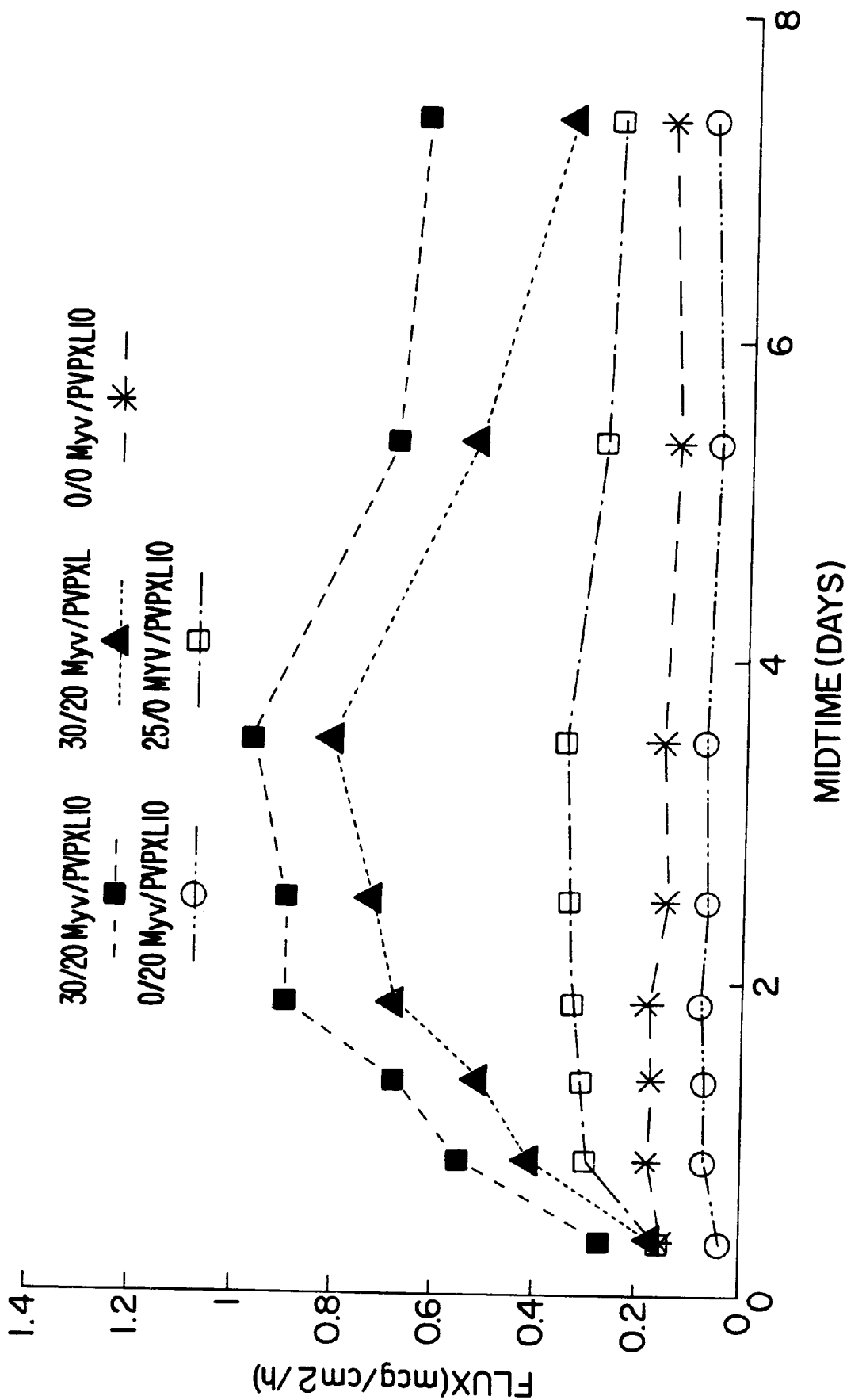

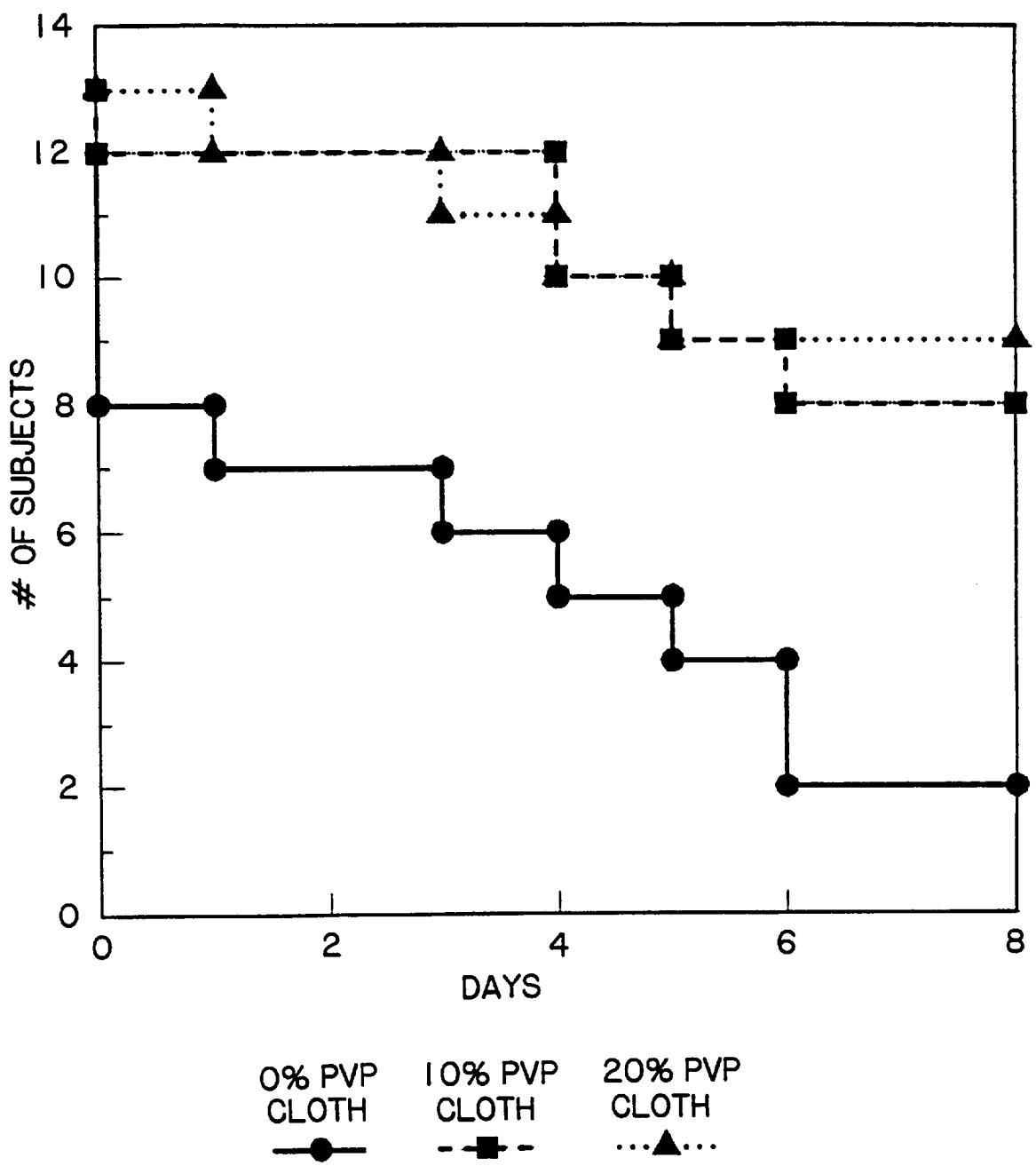

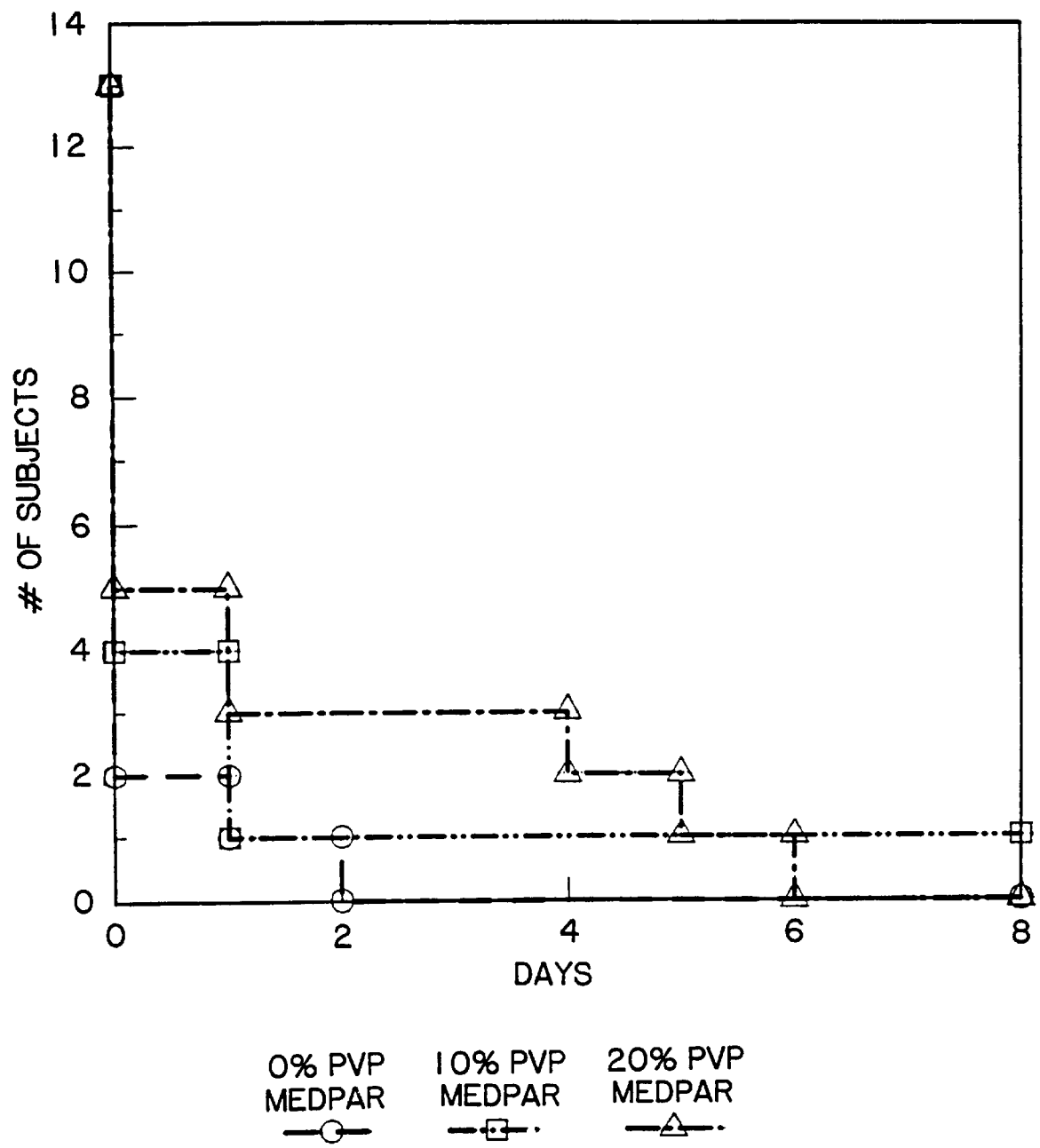

5,919,478

INCORPORATING POLY-N-VINYL AMIDE IN A TRANSDERMAL SYSTEM

This application is a 371 of PCT/US94/07267, filed Jun. 24, 1994, which is a CIP of U.S. Ser. No. 08/082,624, filed Jun. 25, 1993, now abandoned.

TECHNICAL FIELD

This invention relates to the transdermal delivery of drugs and other biologically active agents. More particularly, this invention relates to the transdermal delivery of drugs utilizing a novel combination of a permeation enhancer and a poly-N-vinyl amide to enhance flux, wearability, or stability of a transdermal device.

BACKGROUND ART

The transdermal route of parenteral delivery of drugs provides many advantages over other administrative routes, and transdermal systems for delivering a wide variety of drugs or other beneficial agents are described in U.S. Pat. Nos. 3,598,122; 3,598,123; 3,731,683; 3,797,494; 4,031,894; 4,201,211; 4,286,592; 4,314,557; 4,379,454; 4,435,180; 4,559,222; 4,573,995; 4,588,580; 4,645,502; 4,704,282; 4,788,062; 4,816,258; 4,849,226; 4,908,027; 4,943,435; and 5,004,610, for example. The disclosures of the above patents are incorporated herein by reference. In many instances, drugs that would appear to be ideal candidates for transdermal delivery are found to have such low permeability through intact skin that they cannot be delivered at therapeutically effective rates from reasonably sized systems.

In an effort to increase skin permeability, it has been proposed to pretreat the skin with various chemicals or to concurrently deliver the drug in the presence of a permeation enhancer. Various materials have been suggested for this purpose, as described in U.S. Pat. Nos. 3,472,931, 3,527,864, 3,896,238, 3,903,256, 3,952,099, 4,046,886, 4,130,643, 4,130,667, 4,299,826, 4,335,115, 4,343,798, 4,379,454, 4,405,616 and 4,746,515, all of which are incorporated herein by reference; British Pat. No. 1,001,949; and ldson, Percutaneous Absorption, J. Pharm. Sci., Vol. 64, No. b6, June 1975, pp 901–924 (particularly 919–921).

WO-A-9 307 870 discloses a device for the transdermal delivery administration of melatonin comprising a therapeutically effective amount of melatonin and a skin permeation-enhancing amount of a monoglyceride or mixture of monoglycerides of fatty acids with a total monoesters content of at least 51%.

WO-A-9 308 795 discloses a transdermal therapeutic system comprising a crystallization inhibitor, an active agent, and optionally penetration enhancers, in an adhesive matrix.

EP-A-0 295 411 discloses a pharmaceutical composition for percutaneous administration comprising eperisone, tolperisone, or salts thereof and a monoglyceride of an aliphatic acid having 8 to 12 carbon atoms and/or ester of lactic acid with an aliphatic alcohol having 12 to 18 carbon atoms.

EP-A-0 416 842 discloses a solid matrix system for transdermal drug delivery which may include a water-soluble polymer to improve long term wearing properties by absorbing moisture from the wearer's skin.

Many permeation enhancers interact adversely with other components of transdermal devices. One problem is that many permeation enhancers can partition into other components in the system. This can cause devices to delaminate or it can cause instability of the device, thus shortening its shelf life.

Another problem related to adhesives of transdermal systems is the problem of adhesive failure resulting in water induced fall-off of the system. Adhesive failure may be caused by accumulation of the permeation enhancer at the skin-adhesive interface. As water accumulates on the skin, particularly during exercise or bathing, the interaction between the water and the permeation enhancer causes a soapy solution to form at the interface thereby causing the transdermal system to fall off.

This invention utilizes a novel combination of permeation enhancer(s) and a poly-N-vinyl amide. The novel combination produces a significant and surprising improvement in transdermal fluxes, drug utilization, storage stability, and improved adhesion over previous transdermal devices.

SUMMARY OF THE INVENTION

The present invention comprises a device for the transdermal administration, at a therapeutically effective rate, of a drug, which device comprises a reservoir comprising a therapeutically effective amount of drug, a skin permeation-enhancing amount of a permeation enhancer and a poly-N-vinyl amide; a backing on the skin-distal surface of the reservoir; and means for maintaining the reservoir in drug- and permeation enhancer-transmitting relation with the skin.

The present invention further comprises a device for the transdermal administration, at a therapeutically effective rate, of drug, which device comprises a first reservoir comprising a therapeutically effective amount of drug, a skin permeation-enhancing amount of a permeation enhancer and a poly-N-vinyl amide; a second reservoir comprising a permeation enhancer and a poly-N-vinyl amide, and optionally containing drug; a rate-controlling membrane between the first reservoir and the second reservoir; a backing on the skin-distal surface of the second reservoir; and means for maintaining the first and second reservoirs in drug- and permeation enhancer-transmitting relation with the skin.

The present invention also includes a method for the transdermal administration of a drug, the method comprising the step of placing a transdermal drug delivery device as described above onto the skin of a person.

The present invention also includes a method for increasing the transdermal flux of a drug from a transdermal device comprising incorporating into the drug containing reservoir of the transdermal devices described above, an effective amount of a poly-N-vinyl amide, wherein the device is used in the method for transdermal administration of a drug described above.

The present invention also includes a method for improving the adhesion of a transdermal delivery device comprising incorporating into the drug containing reservoir of the transdermal devices described above, an effective amount of a poly-N-vinyl amide, wherein the transdermal delivery device is used in the method for transdermal administration of a drug described above.

The present invention also includes a method for improving the stability of a transdermal delivery device comprising incorporating into the drug containing reservoir of the transdermal devices described above, an effective amount of a poly-N-vinyl amide, wherein the transdermal delivery device is used in the method for transdermal administration of a drug described above.

BRIEF DESCRIPTION OF THE DRAWINGS

The invention will be described in further detail with reference to the accompanying drawings wherein:

FIG. 1 is a cross-sectional view of one embodiment of the transdermal drug delivery system according to this invention.

FIG. 2 is a cross-sectional view of another embodiment of the transdermal drug delivery system of this invention.

FIG. 3 is a cross-sectional view of still another embodiment of the transdermal drug delivery system according to this invention, utilizing a rate-controlling membrane.

FIG. 13 is a graph showing transdermal flux of ethinyl estradiol across cadaver skin at 35° C. of 2.5% gestodene and 2% ethinyl estradiol with 0% and 20% poly-N-vinyl-2-pyrrolidone.

FIG. 14 is a bar graph showing the effect of poly-N-vinyl-2-pyrrolidone on the transdermal flux across several cadaver skins of 2.5% gestodene.

FIG. 15 is a graph showing transdermal flux of gestodene across cadaver skin at 35° C. of 2.5% gestodene and 2% ethinyl estradiol with 0%, 25% and 30% glycerol monooleate and 0% and 20% poly-N-vinyl-2-pyrrolidone.

FIG. 16 is a graph showing transdermal flux of gestodene across cadaver skin at 35° C. at 2.5% gestodene and 2% ethinyl estradiol with 0%, 25% and 30% glycerol monooleate and 0% and 20% poly-N-vinyl-2-pyrrolidone.

FIG. 17 is a graph showing the effect of poly-N-vinyl-2-pyrrolidone on the wearability of a transdermal system having a cloth backing.

FIG. 18 is a graph showing the effect of poly-N-vinyl-2-pyrrolidone on the wearability of a transdermal system having a medpar backing.

DESCRIPTION OF THE INVENTION

Figure 4:
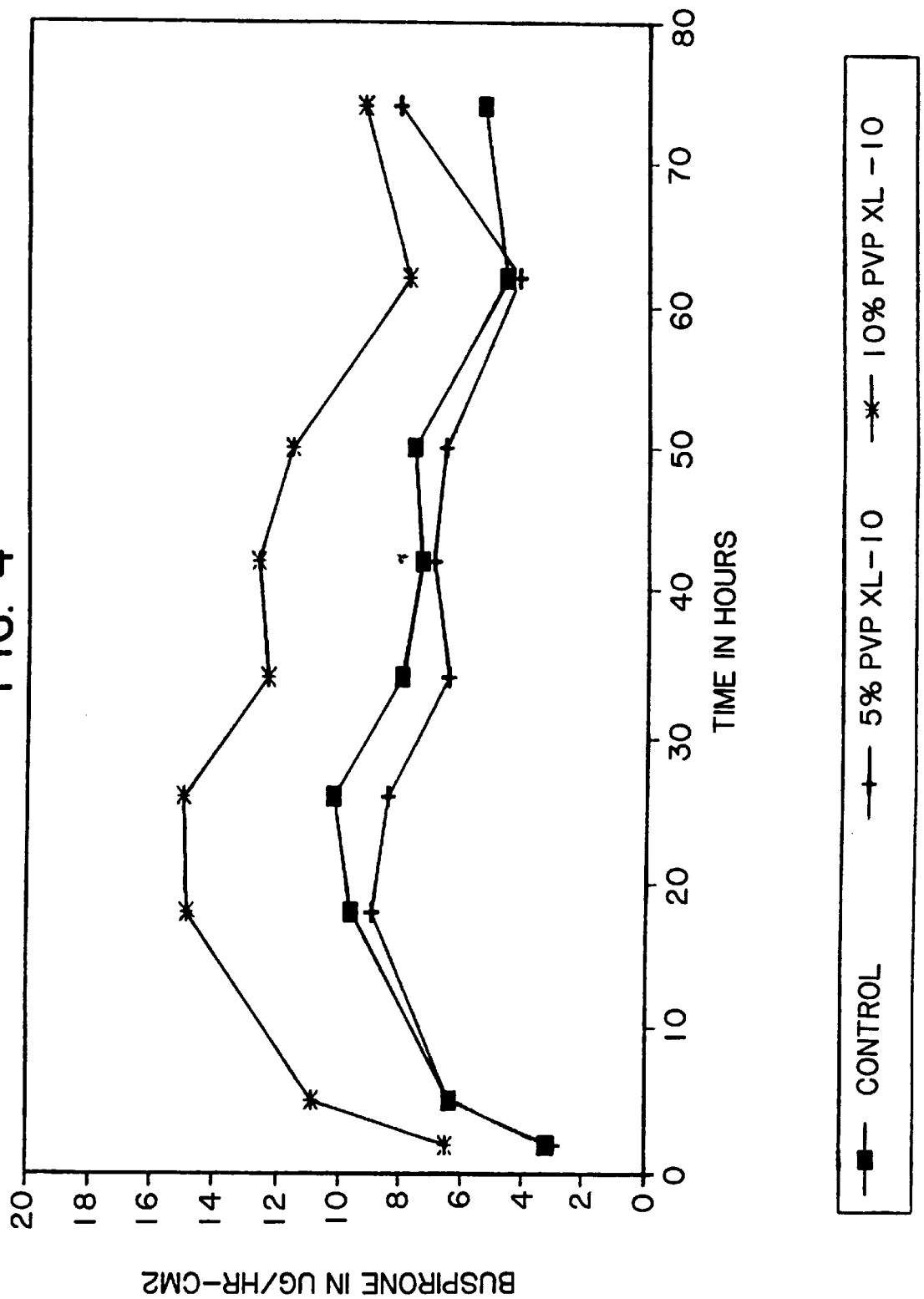
FIG. 4 is a graph showing transdermal flux across cadaver skin at 35° C. of buspirone with 0%, 5% and 10% poly-N-vinyl-2-pyrrolidone.

Examples of suitable transdermal delivery devices are illustrated in FIGS. 1, 2, and 3. The same reference numbers are used throughout the different figures to designate the same or similar components. The figures are not drawn to scale.

In FIG. 1, a preferred embodiment of this invention, transdermal delivery device 10, comprises a matrix reservoir 12 comprising drug, a therapeutically acceptable permeation enhancer and a poly-N-vinyl amide.

Reservoir matrix 12 is sandwiched between a backing layer 14 and an in-line contact adhesive layer 16. The backing layer 14 serves the purpose of preventing passage of drug through the surface of the matrix distant the skin, and also for providing support for the system, where needed.

The device 10 adheres to the surface of the skin 18 by means of the adhesive layer 16. The adhesive layer 16 may optionally contain enhancer and/or drug. The composition and thickness of adhesive layer 16 is selected such that the adhesive does not constitute a significant permeation barrier to the passage of drug. A strippable release liner (not shown in FIG. 1) is normally provided along the exposed surface of adhesive layer 16 and is removed prior to application of device 10 to the skin 18. Preferably, the strippable liner is a siliconized polyester film or fluorocarbon diacrylate film.

Because of the wide variation in skin permeability from individual and from site to site on the same body, it may be preferable that drug and the permeation enhancer be administered from a rate-controlled transdermal delivery device. Rate control can be obtained either through a rate-controlling membrane or adhesive, or through the other means disclosed in the patents noted above. Optionally, a rate-controlling membrane (not shown) may be present between the reservoir matrix 12 and the adhesive layer 16.

Alternatively, as shown in FIG. 2, transdermal therapeutic device 20 may be attached to the skin or mucosa of a patient by means of an adhesive overlay 22. Device 20 is comprised of drug-, permeation enhancer- and poly-N-vinyl amide-containing reservoir matrix 12. A backing layer 14 is provided adjacent one surface of reservoir 12. Adhesive overlay 22 maintains the device on the skin and may be fabricated together with, or provided separately from, the remaining elements of the device. With certain formulations, the adhesive overlay 22 may be preferable to the in-line contact adhesive 16 as shown in FIG. 1. This is true, for example, where the drug/enhancer reservoir contains a material (such as, for example, an oily surfactant permeation enhancer) that adversely affects the adhesive properties of the in-line contact adhesive layer 16. Backing layer 14 is preferably slightly larger than reservoir matrix 12, and in this manner prevents the materials in reservoir 12 from adversely interacting with the adhesive in overlay 22. Optionally, a rate-controlling membrane (not shown in FIG. 2) may be provided on the skin-proximal side of reservoir matrix 12. A strippable release liner 24 is also provided with device 20 and is removed just prior to application of device 20 to the skin.

In FIG. 3, transdermal delivery device 30 comprises a drug-, permeation enhancer- and a poly-N-vinyl amide-containing reservoir matrix 12 substantially as described with respect to FIG. 1. Permeation enhancer reservoir ("enhancer reservoir") 26 comprises a permeation enhancer and a poly-N-vinyl amide dispersed throughout and is optionally containing the drug. Enhancer reservoir 26 is preferably made from substantially the same matrix as is used to form drug reservoir matrix 12. A rate-controlling membrane 28 for controlling the release rate of the permeation enhancer from enhancer reservoir 26 to drug reservoir matrix 12 is placed between the two reservoirs. A rate-controlling membrane (not shown in FIG. 3) for controlling the release rate of the enhancer from drug reservoir matrix 12 to the skin may also optionally be utilized and would be present between adhesive layer 16 and reservoir matrix 12.

Superimposed over the permeation enhancer reservoir 26 of device 30 is a backing 14. On the skin-proximal side of reservoir matrix 12 are an adhesive layer 16 and a strippable liner 24 that would be removed prior to application of the device 30 to the skin.

Suitable materials for the drug matrix include, without limitation, natural and synthetic rubbers or other polymeric materials, thickened mineral oil, or petroleum jelly. A preferred embodiment according to this invention is fabricated from an ethylene/vinyl acetate (EVA) copolymer of the type described in U.S. Pat. No. 4,144,317, incorporated herein in its entirety by reference, preferably those having a vinyl acetate content (VA) in the range of 9 to 60 weight percent and more preferably 28% to 50% VA. Polyisobutylene/oil polymers containing from 4–25% high molecular weight polyisobutylene and 20–80% low molecular weight polyisobutylene with the balance being an oil such as mineral oil or polybutenes may also be used as the matrix material.

The backing layer can be flexible or nonflexible, permeable or impermeable to water vapor, or permeable or impermeable to permeation enhancers. It can have any combination of these characteristics. The backing, however, must be impermeable to drug. Suitable materials include, without limitation, acrylonitrile, cellophane, cellulose acetate, cellulosics, ethylcellulose, ethylene vinyl alcohol, ethylene vinyl acetate, plasticized vinylacetate-vinylchloride copolymers, polyethylene terephthalate, some types of nylons, rayon, polyethylene, polypropylene, polyvinyl alcohol, polyvinyl chloride, metallized polyester films, polyvinylidene chloride, polyester, polycarbonate, polystyrene, polyurethane, aluminum foil, and multi-laminate films. The backing may be a multi-laminate film layer.

The adhesive materials suitable for the present invention include, without limitation, acrylic adhesives, polyisobutylene adhesives, and amine resistant adhesives, such as silicone adhesives. Adhesives disclosed in U.S. Pat. Nos. 3,797,494 and 4,031,894 are incorporated herein by reference. Preferably, the adhesive is an acrylate adhesive.

The rate-controlling membrane may be fabricated from permeable, semipermeable or microporous materials that are known in the art to control the rate of agents into and out of delivery devices. Suitable materials include, but are not limited to, high density polyethylene, low density polyethylene, polyvinyl acetate, polypropylene and ethylene vinyl acetate copolymers.

This invention contemplates the use of materials other than those specifically disclosed herein, including those which may hereafter become known to the art to be capable of performing the necessary functions.

When a constant drug delivery rate is desired, the drug is normally present in the matrix at a concentration in excess of saturation, the amount of excess being a function of the desired length of the drug delivery period of the system. The drug may, however, be present at a level below saturation without departing from this invention as long as drug is continuously administered to the same skin or mucosa site in an amount and for a period of time sufficient to provide the desired therapeutic rate and delivery profile.

The permeation enhancer is dispersed through the matrix or matrices, preferably at a concentration sufficient to provide permeation-enhancing amounts of enhancer in the reservoir throughout the anticipated administration period.

In addition to a drug and a therapeutically acceptable permeation enhancer, the matrix may also contain dyes, pigments, inert fillers, diluents, antioxidants, antibacterials, stabilizers, vehicles, anesthetics, rubefacients, antipruritics, gelling agents, excipients and other conventional components of pharmaceutical products or transdermal devices known to the art.

In a preferred embodiment of this invention, reservoir matrix 12 comprises 30 to 70 weight percent polymer (preferably 28 to 50 percent), 1 to 40 weight percent drug (preferably 5 to 25 weight percent), 1 to 50 weight percent permeation enhancer (preferably 10 to 40 weight percent), and 5 to 40 weight percent poly-N-vinyl amide (preferably 10 to 25 weight percent).

In a preferred embodiment of this invention, reservoir matrix 12 comprises 30 to 70 weight percent ethylene vinyl acetate copolymer having a 9 to 60 percent vinyl acetate content (preferably 28 to 50 percent), 1 to 40 weight percent drug (preferably 5 to 25 weight percent), 1 to 50 weight percent permeation enhancer (preferably 10 to 40 weight percent), and 5 to 40 weight percent poly-N-vinyl amide (preferably 10 to 25 weight percent), preferably poly-N-vinyl-2-pyrrolidone.

In a preferred embodiment of this invention, reservoir matrix 12 comprises 30 to 70 weight percent ethylene vinyl acetate copolymer having a 9 to 60 percent vinyl acetate content (preferably 28 to 50 percent), 1 to 40 weight percent drug (preferably 5 to 25 weight percent), 5 to 40 percent lactic ester of an alcohol (preferably 10 to 30 weight percent), preferably lauryl lactate, 1 to 30 weight percent monoglyceride or mixture of monoglycerides of a fatty acid (preferably 5 to 25 weight percent), preferably glycerol monolaurate or glycerol monooleate, and 5 to 40 weight percent poly-N-vinyl amide (preferably 10 to 25 weight percent), preferably N-vinyl-2-pyrrolidone.

In a preferred embodiment of this invention, reservoir matrix 12 comprises 30 to 70 weight percent ethylene vinyl acetate copolymer having a 9 to 60 percent vinyl acetate content (preferably 28 to 50 percent), 1 to 40 weight percent drug (preferably 5 to 25 weight percent), 1 to 30 weight percent monoglyceride or mixture of monoglycerides of a fatty acid (preferably 5 to 25 weight percent), preferably glycerol monolaurate or glycerol monooleate, and 5 to 40 weight percent poly-N-vinyl amide (preferably 10 to 25 weight percent), preferably N-vinyl-2-pyrrolidone.

The devices of this invention can be designed to effectively deliver drug for an extended time period of from several hours up to 7 days or longer.

The administration rate of the drug through the skin should be sufficient to minimize the size of the device. The size of the device of this invention can vary from 1 $cm^2$ to greater than 200 $cm^2$. A typical device, however, will have a size within the range of 5–50 $cm^2$. The transdermal therapeutic devices of the present invention are prepared in a manner known in the art, such as by those procedures, for example, described in the transdermal device patents listed previously herein.

This invention finds particular usefulness both in enhancing permeability across skin and in increasing the wearability, ie, improving the adhesion, of a transdermal device. It is also useful in enhancing flux across mucosa. Further, this invention is useful in delivery of both systemically and topically active drugs. According to our invention, the permeation-enhancing mixture and the drug to be delivered are placed in drug- and permeation-enhancing mixture-transmitting relationship to the appropriate body surface, and maintained in place for the desired period of time.

The method for the transdermal administration of a drug of this invention comprises administering a drug, in a therapeutically effective amount, to the area of skin over the time period and coadministering a permeation-enhancing mixture according to this invention to the area of skin from a polymer matrix containing a poly-N-vinyl amide.

The method for increasing the transdermal flux of a drug from a transdermal device made according to this invention comprises incorporating into a polymer matrix of a reservoir of a transdermal device, wherein the reservoir also contains a therapeutically effective amount of a drug to be administered and a permeation-enhancing mixture, an effective amount, of a poly-N-vinyl amide, preferably 5 to 40 weight percent, most preferably 10 to 25 weight percent, wherein the poly-N-vinyl amide is preferably poly-N-vinyl-2-pyrrolidone, and transdermally administering the drug in accordance with the teachings of this invention.

The method for improving the adhesion of a transdermal device made according to this invention comprises incorporating into a polymer matrix of a reservoir of a transdermal device, wherein the reservoir also contains a therapeutically effective amount of a drug to be administered and a permeation-enhancing mixture, an effective amount, of a poly-N-vinyl amide, preferably 5 to 40 weight percent, most preferably 10 to 25 weight percent, wherein the poly-N-vinyl amide is preferably poly-N-vinyl-2-pyrrolidone, and transdermally administering the drug in accordance with the teachings of this invention.

The method for improving the stability of a transdermal device made according to this invention comprises incorporating into a polymer matrix of a reservoir of a transdermal device, wherein the reservoir also contains a therapeutically effective amount of a drug to be administered and a permeation-enhancing mixture, an effective amount, of a poly-N-vinyl amide, preferably 5 to 40 weight percent, most preferably 10 to 25 weight percent, wherein the poly-N-vinyl amide is preferably poly-N-vinyl-2-pyrrolidone, and transdermally administering the drug in accordance with the teachings of this invention.

It is believed that this invention has utility in connection with the delivery of drugs within the broad class normally delivered through body surfaces and membranes, including skin. As used herein, the expressions "drug" and "agent" are used interchangeably and are intended to have their broadest interpretation as to any therapeutically active substance that is delivered to a living organism to produce a desired, usually beneficial, effect. In general, this includes therapeutic agents in all of the major therapeutic areas, including, but not limited to, ACE inhibitors, adenohypophyseal hormones, adrenergic neuron blocking agents, adrenocortical steroids, inhibitors of the biosynthesis of adrenocortical steroids, alpha-adrenergic agonists, alpha-adrenergic antagonists, selective alpha-two-adrenergic agonists, analgesics, antipyretics and anti-inflammatory agents, androgens, local anesthetics, general anesthetics, antiaddictive agents, antiandrogens, antiarrhythmic agents, antiasthmatic agents, anticholinergic agents, anticholinesterase agents, anticoagulants, antidiabetic agents, antidiarrheal agents, antidiuretic, antiemetic and prokinetic agents, antiepileptic agents, antiestrogens, antifungal agents, antihypertensive agents, antimicrobial agents, antimigraine agents, antimuscarinic agents, antineoplastic agents, antiparasitic agents, antiparkinson's agents, antiplatelet agents, antiprogestins, antithyroid agents, antitussives, antiviral agents, atypical antidepressants, azaspirodecanediones, barbiturates, benzodiazepines, benzothiadiazines, beta-adrenergic agonists, beta-adrenergic antagonists, selective beta-one-adrenergic antagonists, selective beta-two-adrenergic agonists, bile salts, agents affecting volume and composition of body fluids, butyrophenones, agents affecting calcification, calcium channel blockers, cardiovascular drugs, catecholamines and sympathomimetic drugs, cholinergic agonists, cholinesterase reactivators, dermatological agents, diphenylbutylpiperidines, diuretics, ergot alkaloids, estrogens, ganglionic blocking agents, ganglionic stimulating agents, hydantoins, agents for control of gastric acidity and treatment of peptic ulcers, hematopoietic agents, histamines, histamine antagonists, 5-hydroxytryptamine antagonists, drugs for the treatment of hyperlipoproteinemia, hypnotics and sedatives, immunosuppressive agents, laxatives, methylxanthines, monoamine oxidase inhibitors, neuromuscular blocking agents, organic nitrates, opioid analgesics and antagonists, pancreatic enzymes, phenothiazines, progestins, prostaglandins, agents for the treatment of psychiatric disorders, retinoids, sodium channel blockers, agents for spasticity and acute muscle spasms, succinimides, thioxanthenes, thrombolytic agents, thyroid agents, tricyclic antidepressants, inhibitors of tubular transport of organic compounds, drugs affecting uterine motility, vasodilators, vitamins and the like.

In operation, device 10 is applied to a relatively nonhairy area of the skin that is preferably substantially free of wrinkles, creases or folds. Various locations on the torso, such as the flank or shoulder, provide suitable sites for the transdermal system. Once the device is placed on the skin, it will begin administering drug to the wearer.

A certain amount of drug will bind to the skin, and it is accordingly preferred that the skin-contacting layer of the device include this amount of the agent as a loading dose.

Typically, the system is applied for 16 hours to 7 days. The system application is easily adapted for various duration treatments, but generally 24 to 72 hours is the nominal duration for treatment of a single dose.

As used herein, the term "therapeutically effective" amount or rate refers to the amount or rate of drug or active agent needed to effect the desired therapeutic result. The amount of drug present in the therapeutic device and required to achieve a therapeutically effective result depends on many factors, such as the minimum necessary dosage of drug for the particular indication being treated; the solubility in the matrix and permeability through the matrix, of the adhesive layer and of the rate-controlling membrane, if present; and the period of time for which the device will be fixed to the skin. The minimum amount of drug is determined by the requirement that sufficient quantities of drug must be present in the device to maintain the desired rate of release over the given period of application. The maximum amount for safety purposes is determined by the requirement that the quantity of drug present cannot exceed a rate of release that reaches toxic levels.

As used herein, the term "skin permeation-enhancing" amount refers to the amount of permeation enhancer needed to effect the desired therapeutic result. The amount of permeation enhancer present in the therapeutic device and required to achieve a therapeutically effective result depends on many factors, such as the minimum necessary dosage of drug for the particular indication being treated; the solubility of the drug and permeation enhancer in the matrix and permeability through the matrix, of the adhesive layer and of the rate-controlling membrane, if present; and the period of time for which the device will be fixed to the skin. The minimum amount of permeation enhancer is determined by the requirement that sufficient quantities of permeation enhancer must be present in the device to maintain the desired rate of drug release over the given period of application. The maximum amount for safety purposes is determined by the requirement that the quantity of permeation enhancer present cannot exceed a rate of release that causes irritation or causes the drug level to reach toxic levels.

As used herein, the term "flux enhancing amount" refers to the amount of poly-N-vinyl amide present in the therapeutic device required to produce an improvement in transdermal fluxes, storage stability, or drug utilization of the device over an identical device containing no poly-N-vinyl amide. The amount depends on the solubility of the permeation enhancer in the poly-N-vinyl amide.

As used herein, the term "adhesion-improving amount" refers to the amount of poly-N-vinyl amide present in the therapeutic device required to produce an improvement in the wearability, storage stability or drug utilization of the device over an identical device containing no poly-N-vinyl amide.

As used herein, the term "stability-improving amount" refers to the amount of poly-N-vinyl amide present in the therapeutic device required to produce an improvement in the wearability, storage stability or drug utilization of the device over an identical device containing no poly-N-vinyl amide.

As used herein the term "therapeutically acceptable permeation enhancer" means a monoglyceride or mixture of monoglycerides of a fatty acid; a dimethyl alkylamide; a sucrose ester or a mixture of sucrose esters of a fatty acid; a lactic ester of an alcohol; a polyethylene glycol ester of a fatty acid; a benzoic acid of a fatty acid ester; an alkyl laurate; a diethanolamide of a fatty acid; and the like, and combinations thereof. The presently preferred permeation enhancers of the present invention are monoglyceride or mixture of monoglycerides of fatty acids and a lactic ester of an alcohol, either alone or in combination. The most preferred permeation enhancers are glycerol monolaurate, glycerol monooleate, and lauryl lactate, either alone or in combination.

As used herein the term "poly-N-vinyl amide" means a poly-N-vinyl amide or combination of poly-N-vinyl amide such as poly-N-vinylmethylacetamide, poly-N-vinylethylacetamide, poly-N-vinylmethyl-isobutyramide, poly-N-vinyl-2-pyrrolidone, poly-N-vinylpyrrolidone, poly-N-vinyl-2-piperidone, poly-N-vinyl-caprolactam, poly-N-vinyl-5-methyl-2-pyrrolidone, poly-N-vinyl-3-methyl-2-pyrrolidone, and the like. Preferably, the poly-N-vinyl amide is poly-N-vinyl-2-pyrrolidone (more preferably Polyplasdone XL®, Polyplasdone XL-10®, GAF) having a molecular weight of 10,000 to 5,000,000 Daltons and a particle size from 0.1 to 1000 µm.

As used herein, the term "transdermal" delivery or application refers to the delivery or application of drug by passage through skin, mucosa and/or other body surfaces by topical application.

As used herein, the term "substantial portion of the time period" means at least 60% of the time period, preferably at least 90% of the time period. Correlatively, the term "substantially constant" means a variation of less than ±20%, preferably less than ±10%, over a substantial portion of the time period.

As used herein, the term "extended period of time" or "extended time period" means at least 16 hours.

As used herein, the term "a monoglyceride or mixture of monoglycerides of fatty acids" has a total monoesters content of at least 51%, where the monoesters are those with from six to twenty carbon atoms, such as glycerol monooleate, glycerol monolaurate and glycerol monolinoleate.

As used herein, the term "fatty acids" refers to fatty acids that are saturated or unsaturated and straight or chained, and include, for example, lauric acid, myristic acid, stearic acid, oleic acid, linoleic acid and palmitic acid.

As used herein, the term "dimethyl alkylamide" refers to an alkyl having 1 to 18 carbon atoms, preferably eight to sixteen carbon atoms, such as dimethyl lauramide.

As used herein, the term "sucrose ester or a mixture of sucrose esters of a fatty acid" refers to a fatty acid having six to twenty carbon atoms, such as sucrose monococoate.

As used herein, the term "lactic ester of an alcohol" refers to an alcohol having two to eighteen carbon atoms, such as lauryl lactate, ethyl lactate, cetyl lactate and myristyl lactate.

As used herein, the term "polyethylene glycol ester of a fatty acid" refers to a polyethylene glycol having an average molecular weight of 50 to 1000 and a fatty acid having from six to twenty carbon atoms, such as polyethylene glycol-200 monolaurate and polyethylene glycol-400 monolaurate.

As used herein, the term "benzoic acid of a fatty acid ester" refers to a fatty acid having from eight to eighteen carbon atoms, such as isoestearyl benzoate.

As used herein, the term "alkyl laurate" refers to an alkyl having from two to eight carbon atoms, such as ethyl laurate.

As used herein, the term "diethanolamide of a fatty acid" refers to an amide, such as lauramide diethanolamide or cocamide diethanolamide, formed by a condensation reaction between a fatty acid having eight to eighteen carbon atoms, preferably ten to sixteen carbon atoms, and diethanolamine.

As used herein, the term "glycerol monooleate" refers to glycerol monooleate itself or a mixture of glycerides wherein glycerol monooleate is present in the greatest amount.

As used herein, the term "glycerol monolaurate" refers to glycerol monolaurate itself or a mixture of glycerides wherein glycerol monolaurate is present in the greatest amount.

As used herein, the term "glycerol monolinoleate" refers to glycerol monolinoleate itself or a mixture of glycerides wherein glycerol monolinoleate is present in the greatest amount.

The following examples are offered to illustrate the practice of the present invention and are not intended to limit the invention in any manner.

EXAMPLE 1

The drug/permeation enhancer reservoir was prepared by mixing ethylene vinyl acetate having a vinyl acetate content of 40 percent ("EVA 40", U.S.I. Chemicals, Illinois) and N-vinyl-2-pyrrolidone (Polyplasdone XL-10®, GAF), if present, in an internal mixer (Bra Bender type mixer) until the EVA 40 pellets fused. Buspirone and glycerol monooleate were then added. The mixture was blended for approximately 20 minutes at 54°–56° C. and 30 rpm. After blending, the mixture was quickly cooled to 40°–45° C., and calendered to a 2.8–4.0 mil thick film. The compositions of the reservoirs are given in Table 1.

TABLE 1

Drug/Permeation Enhancer Reservoir Composition
(weight percent)

buspirone/glycerol monooleate/EVA 40
(20/20/60)
buspirone/glycerol monooleate/EVA 40/
N-vinyl-2-pyrrolidone
(20/20/55/5)
buspirone/glycerol monooleate/EVA 40/
N-vinyl-2-pyrrolidone
(20/20/50/10)

The film was then laminated to an acrylate contact adhesive (MSP041991P, 3M) on one side and Medpar® backing (3M) on the opposite side. The laminate was then cut into circles using a stainless steel punch.

For each device tested, the adhesive was placed against the stratum corneum side of a disc of epidermis that had been blotted dry just prior to use. The excess epidermis was wrapped around the device so that none of the device edge was exposed to the receptor solution.

The device covered with epidermis was attached to the flat side of the Teflon holder of a release rate rod using nylon netting and nickel wire. The rods were reciprocated in a fixed volume of receptor solution (distilled water). The entire receptor solution was changed at each sampling time. The temperature of the water bath was maintained at 35° C.

The receptor solutions were stored in capped vials at room temperature until assayed for buspirone content by HPLC. The fluxes achieved for the different systems are shown in FIG. 4. As can be seen from FIG. 4, the drug fluxes for the systems containing 10% N-vinyl-2-pyrrolidone were higher than the drug fluxes for the systems containing no N-vinyl-2-pyrrolidone.

EXAMPLE 2

The drug/permeation enhancer reservoir was prepared by mixing ethylene vinyl acetate having a vinyl acetate content of 40% ("EVA 40", U.S.I. Chemicals, Illinois) and N-vinyl-2-pyrrolidone (Polyplasdone XL-10®, GAF), if present, in an internal mixer ((Bra Bender type mixer) until the EVA 40 pellets fused. Melatonin and glycerol monooleate were then added. The mixture was blended for approximately 20 minutes at 54–56° C. and 30 rpm. After blending, the mixture was quickly cooled to 40°–45° C., and calendered to a 4 mil thick film. The compositions of the reservoirs are given in Table 2.

TABLE 2

Drug/Permeation Enhancer Reservoir Composition
(weight percent)

EVA 40/glycerol monooleate/melatonin
(64/30/6)
EVA 40/glycerol monooleate/melatonin/N-vinyl-2-
pyrrolidone
(44/30/6/20)
EVA 40/glycerol monooleate/melatonin
(60/30/10)
EVA 40/glycerol monooleate/melatonin/N-vinyl-2-
pyrrolidone
(40/30/10/20)

The films were then laminated to an acrylate contact adhesive (80912 CN 396791, 3M) on one side and a nylon reinforced polyurethane backing NRU-100-c (80931) on the opposite side. The film were then punched into ⅝" diameter disks using a stainless steel punch and taped to prevent edge release.

For each device tested, the adhesive were placed against the stratum corneum side of a disc of epidermis that had been blotted dry prior to use. The excess epidermis was then wrapped around the device.

The device covered with epidermis was attached to the flat side of the teflon holder of a release rate rod using nylon netting and nickel wire. The rods were reciprocated in a fixed volume of receptor solution (distilled water). The entire receptor solution was changed at each sampling time. The temperature of the water level was maintained at 35° C.

Figure 5:
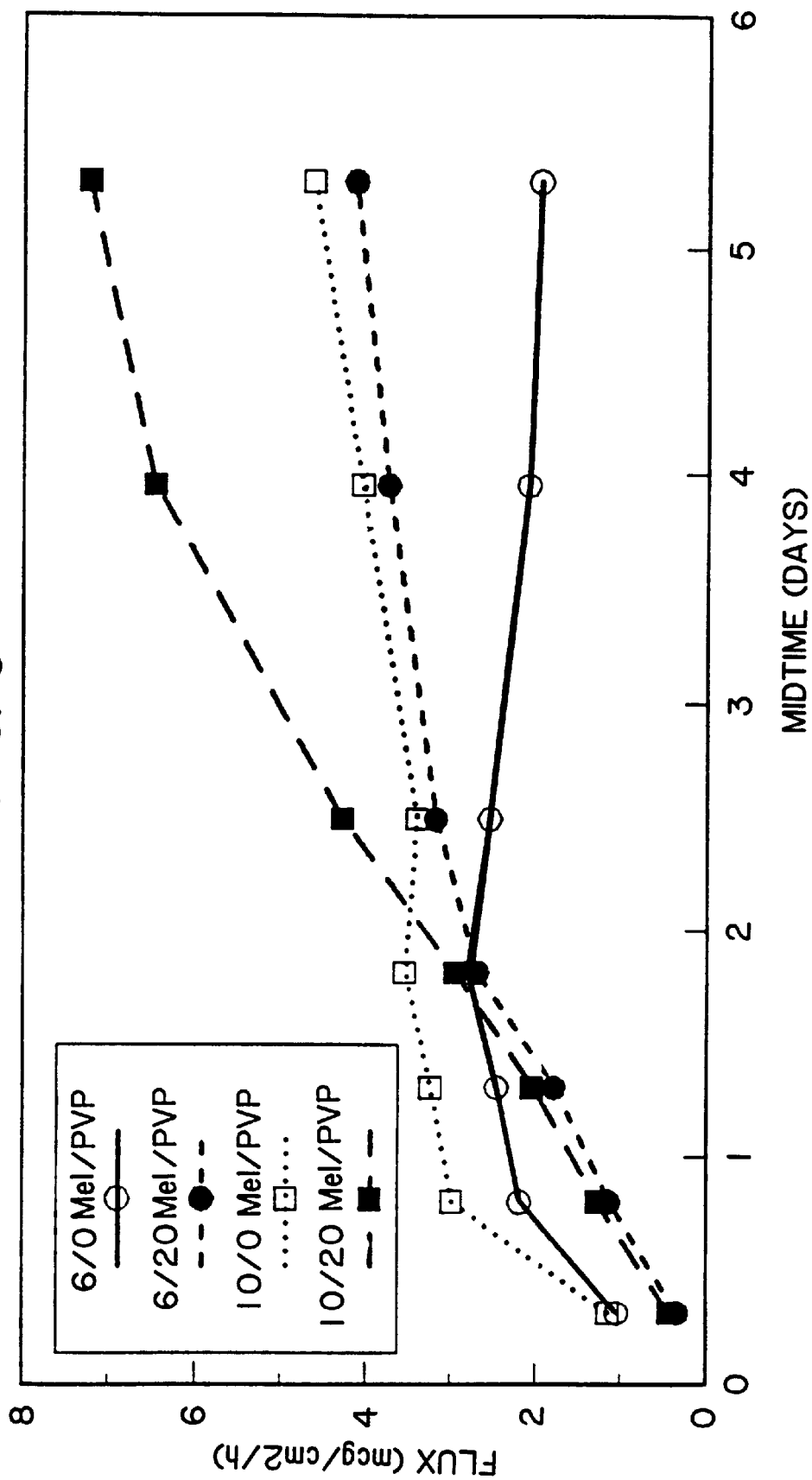
FIG. 5 is a graph showing transdermal flux across cadaver skin at 35° C. of 6% and 10% melatonin with 0% and 20% poly-N-vinyl-2-pyrrolidone.

The receptor solutions were stored in capped vials at room temperature until assayed for melatonin content by HPLC. The fluxes achieved for the different systems are shown in FIG. 5. As can be seen from FIG. 5, the drug fluxes for the systems containing 20% N-vinyl-2-pyrrolidone were higher than the drug fluxes for the systems that contained no N-vinyl-2-pyrrolidone.

EXAMPLE 3

The drug/permeation enhancer reservoir was prepared by mixing ethylene vinyl acetate having a vinyl acetate content or 40% ("EVA 40", U.S. Chemicals, Illinois) and N-vinyl-2-pyrrolidone (Polyplasdone XL-10®, GAF) if present, in an internal mixer (Bra Bender type mixer) until the EVA 40 pellets fused. Tacrine and glycerol monooleate were then added. The mixture was blended for approximately 20 minutes at 54–56° C. and 30 rpm. After blending the mixture was quickly cooled to 40–45° C., and calendered to 4 mil thick film. The compositions of the reservoirs are given in Table 3.

TABLE 3

Drug/Permeation Enhancer Reservoir Composition
(weight percent)

tacrine/glycerol monooleate/EVA 40
(4/30/66)
tacrine/glycerol monooleate/EVA 40/N-vinyl-2-pyrrolidone
(4/30/46/20)
tacrine/glycerol monooleate/EVA 40
(6/30/64)
tacrine/glycerol monooleate/EVA 40/N-vinyl-2-pyrrolidone
(6/30/44/20)

The films were laminated to an acrylate contact adhesive (80912 CN 396791, 3M) on one side and a nylon reinforced polyurethane backing (NRU-100-c) (80931) on the opposite side. The films were then cut into circles using a stainless steel punch and taped to prevent edge release.

For each device tested, the adhesive were placed against the stratum corneum side of a disc of epidermis that had been blotted dry just prior to use. The excess epidermis was then wrapped around the device.

The device covered with epidermis was attached to the flat side of the teflon holder of a release rate rod using nylon netting and nickel wire. The rods were reciprocated in a fixed volume of receptor solution (0.05 M phosphate at pH 4). The entire receptor solution was changed at each sampling time. The temperature of the water bath was maintained at 35° C.

Figure 6:
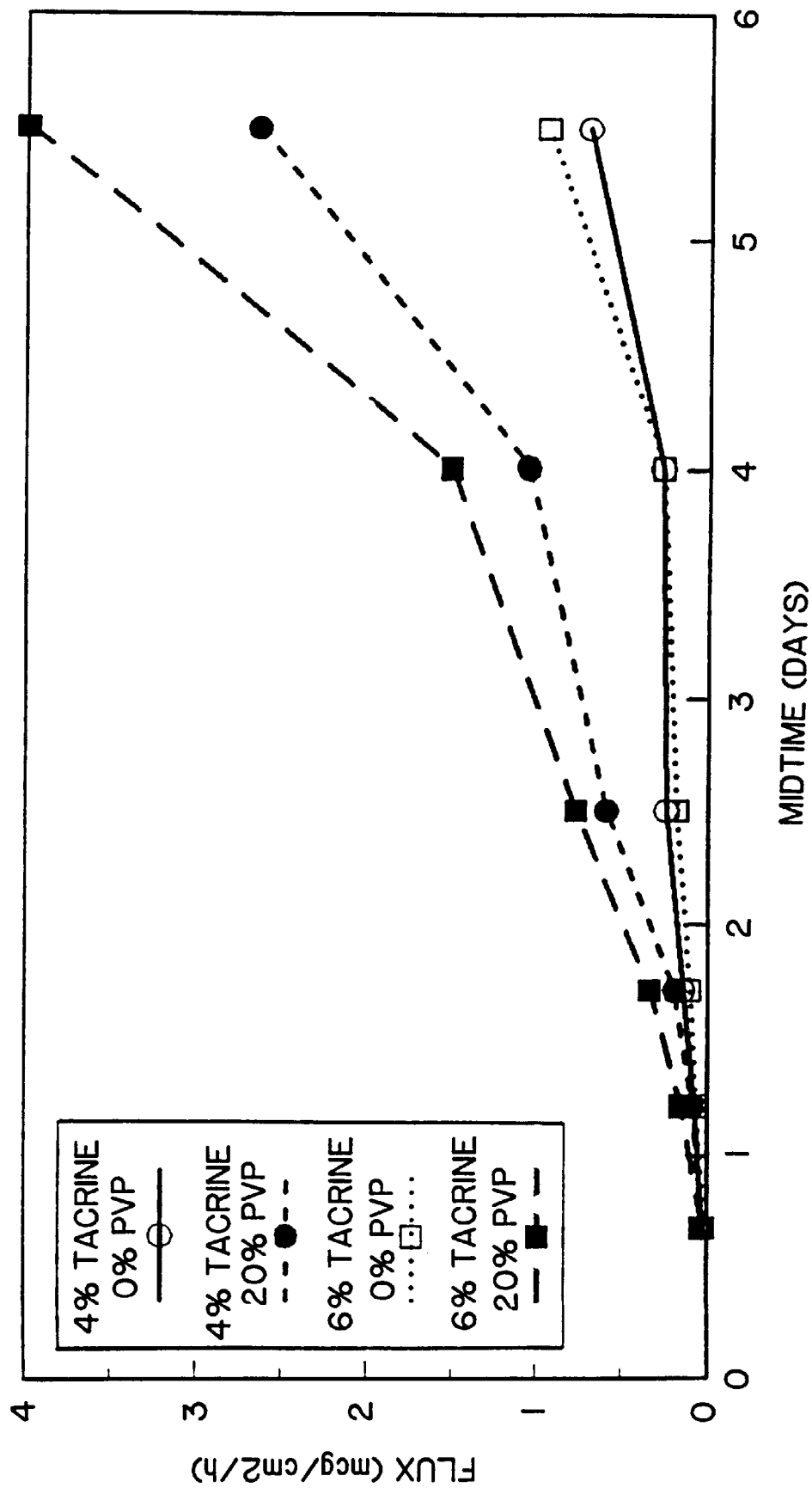
FIG. 6 is a graph showing transdermal flux across cadaver skin at 35° C. of 4% and 6% tacrine with 0% and 20% poly-N-vinyl-2-pyrrolidone.

The receptor solutions were stored in capped vials at room temperature until assayed for tacrine content by HPLC. The fluxes achieved for the different systems are shown in FIG. 6. As can be seen from FIG. 6, the drug fluxes for the systems containing 20% N-vinyl-2-pyrrolidone were higher than the drug fluxes for the systems that contained no N-vinyl-2-pyrrolidone.

EXAMPLE 4

The drug/permeation enhancer reservoir was prepared by mixing ethylene vinyl acetate having a vinyl acetate content of 40 percent ("EVA 40", U.S.I. Chemicals, Illinois) and N-vinyl-2-pyrrolidone (Polyplasdone XL-10®, GAF) if present, in an internal mixer (Bra Bender type mixer) until the EVA 40 pellets fused. Testosterone and glycerol monooleate were then added. The mixture was blended for approximately 20 minutes at 54–56° C. at 30 rpm. After blending the mixture was quickly cooled to 40–45° C., and calendered to a 4 mil thick film. The compositions of the reservoirs are given in Table 4.

TABLE 4

Drug/Permeation Enhancer Reservoir Composition
(weight percent)

testosterone/glycerol monooleate/EVA 40
(10/30/60)
testosterone/glycerol monooleate/EVA 40/N-vinyl-2-
pyrrolidone
(10/30/40/20)
testosterone/glycerol monooleate/EVA 40
(12/30/58)
testosterone/glycerol monooleate/EVA 40/N-vinyl-2-
pyrrolidone
(12/30/38/20)

The films were then laminated to an acrylate contact adhesive (code 80912, CN396791, 3M) on one side and a nylon reinforced polyurethane backing NRU-100-c (code 80931) on the opposite side. The films were then cut into circles using a stainless steel punch and taped to prevent edge release.

For each device tested, the adhesive was placed against the stratum corneum side of a disc of epidermis that had been blotted dry just prior to use. The excess epidermis was then wrapped around the device.

The device covered with epidermis was attached to the flat side of the Teflon holder of a release rate rod using nylon netting and nickel wire. The rods were reciprocated in a fixed volume of receptor solution (0.1% benzoic acid). The entire receptor solution was changed at each sampling time. The temperature of the water bath was maintained at 35° C.

Figure 7:
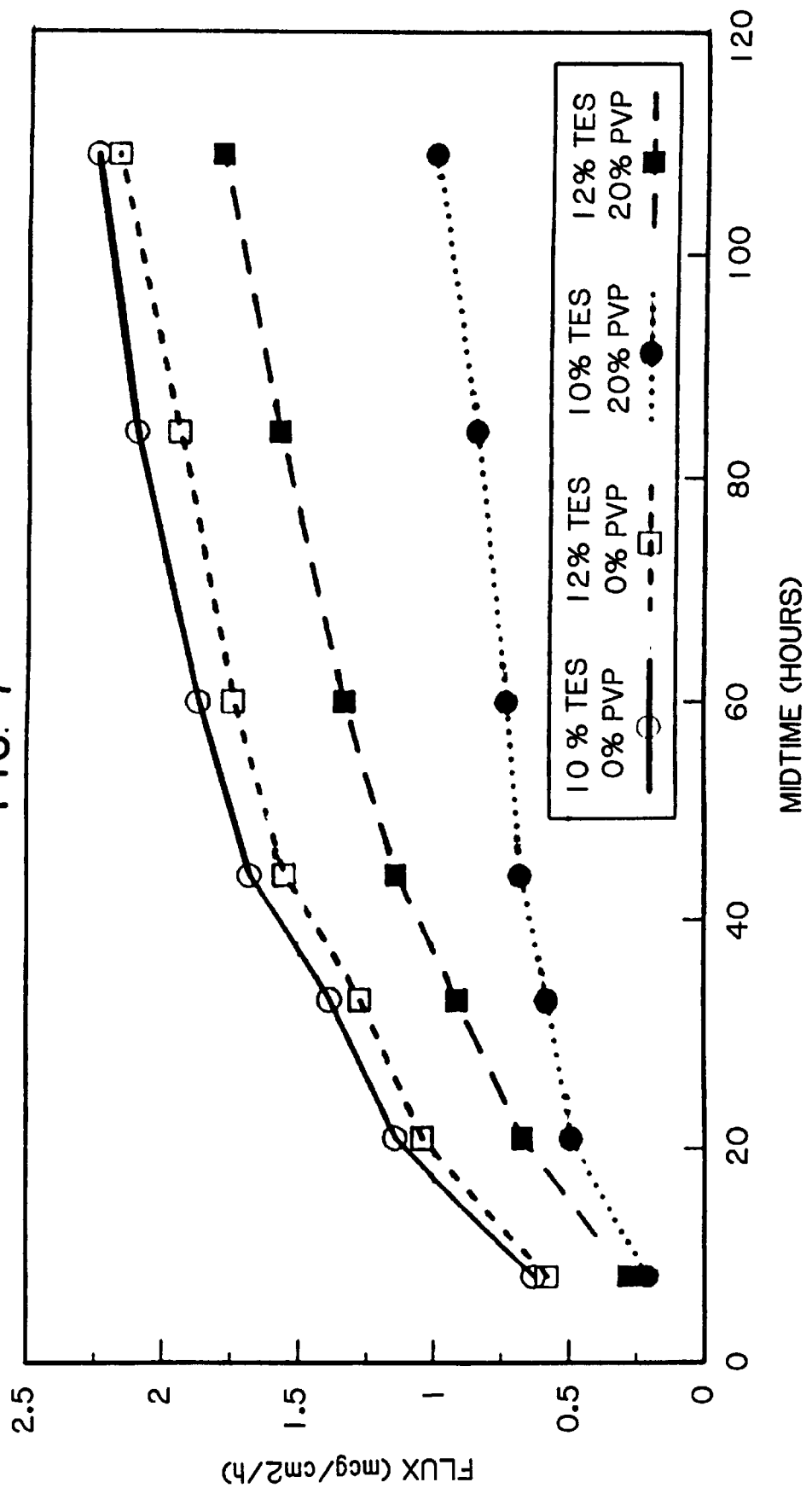
FIG. 7 is a graph showing transdermal flux across cadaver skin at 35° C. of 10% and 12% testosterone with 0% and 20% poly-N-vinyl-2-pyrrolidone.

The receptor solutions were stored in capped vials at room temperature until assayed for testosterone content by HPLC. The fluxes achieved for the different systems are shown in FIG. 7. As can be seen from FIG. 7, the drug fluxes for the systems containing 20% N-vinyl pyrrolidone were higher than the drug fluxes for the systems containing no N-vinyl-2-pyrrolidone.

EXAMPLE 5

The drug/permeation enhancer reservoir were prepared by mixing ethylene vinyl acetate having a vinyl acetate content of 40 percent ("EVA 40", U.S.I. Chemicals, Illinois) and N-vinyl-2-pyrrolidone (Polyplasdone XL-10®, GAF), if present, in an internal mixer (Bra Bender type mixer) until the EVA 40 pellets fused. Alprazolam and glycerol monooleate were then added. The mixture was blended for approximately 20 minutes at 54–56° C. and 30 rpm. After blending, the mixture was quickly cooled to 40–45° C. and calendered to a 4 mil thick film. The compositions of the reservoirs are given in Table 5.

TABLE 5

Drug/Permeation Enhancer Reservoir Composition
(weight percent)

alprazolam/glycerol monooleate/EVA 40
(2/30/68)
alprazolam/glycerol monooleate/EVA 40/N-vinyl-2-
pyrrolidone
(2/30/48/20)
alprazolam/glycerol monooleate/EVA 40
(4/30/66)
alprazolam/glycerol monooleate/EVA 40/N-vinyl-2-
pyrrolidone
(4/30/46/20)

The films were then laminated to an acrylate contact adhesive (80912 CN 396791, 3M) on one side and a NRU-100-c (80931) backing on the opposite side. The films were then cut into circles using a stainless steel punch and taped to prevent edge release.

For each device tested, the adhesive was placed against the stratum corneum side of a disc of epidermis that had been blotted dry just prior to use. The excess epidermis was then wrapped around the device.

The device covered with epidermis was attached to the flat side of the Teflon holder of a release rate rod using nylon netting and nickel wire. The rods were reciprocated in a fixed volume of receptor solution (0.01 M phosphate buffer at pH 6). The entire receptor solution was changed at each sampling time. The temperature of the water bath was maintained at 35° C.

Figure 8:
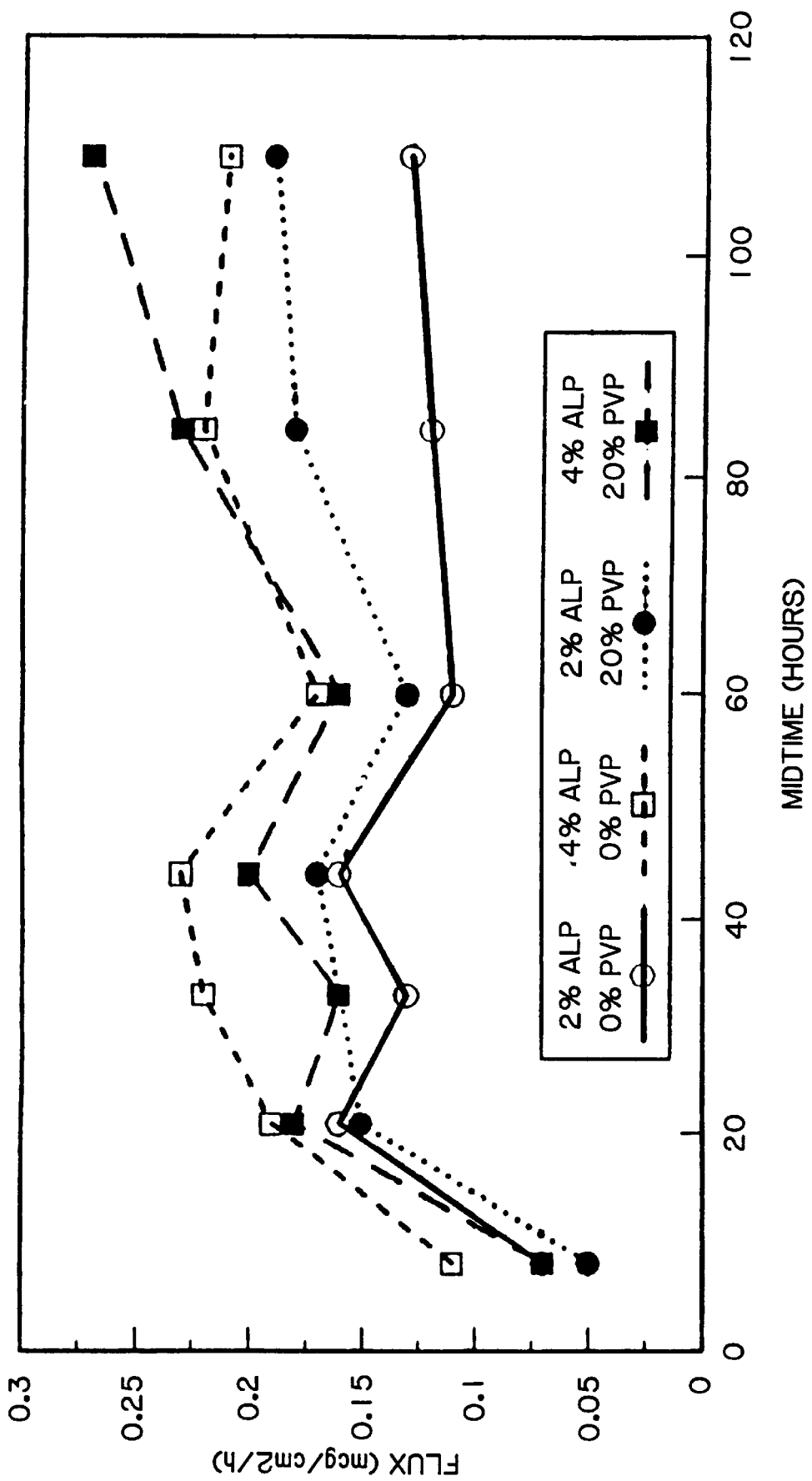
FIG. 8 is a graph showing transdermal flux across cadaver skin at 35° C. of 2% and 4% alprazolam with 0% and 20% poly-N-vinyl -2-pyrrolidone.

The receptor solutions were stored in capped vials at room temperature until assayed for alprazolam content by HPLC. The fluxes achieved for the different systems are shown in FIG. 8.

EXAMPLE 6

The drug/permeation enhancer reservoir was prepared by mixing ethylene vinyl acetate having a vinyl acetate content of 33 percent ("EVA 33", U.S.I. Chemicals, Illinois) and N-vinyl-2-pyrrolidone (Polyplasdone XL-10®, GAF), if present, in an internal mixer (Bra Bender type mixer) until the EVA 33 pellets fused. Gestodene, ethinyl estradiol and glycerol monooleate were then added. The mixture was blended, and calendered to a 4 mil thick film. The compositions of the reservoirs are given in Table 6.

TABLE 6

Drug/Permeation Enhancer Reservoir Composition
(weight percent)

ethinyl estradiol/gestodene/glycerol monooleate/EVA 33
(2/2.5/23.9/71.6)
ethinyl estradiol/gestodene/glycerol monooleate/EVA
33/N-vinyl-2-pyrrolidone (2/2.5/23.9/56.6/15)
ethinyl estradiol/gestodene/glycerol monooleate/EVA
33/N-vinyl-2-pyrrolidone (2/2.5/23.9/51.6/20)

This film was then laminated to an acrylate contact adhesive (147-123-4, Adhesive Research Co.) on one side and a nylon reinforced polyurethane backing NRU-100-c® (code 80931) (Flexcon Co.) on the opposite side. The film was then cut into circles and taped to prevent edge release.

For each device tested, the adhesive was placed against the stratum corneum side of a disc of human epidermis that had been blotted dry just prior to use. The excess epidermis was wrapped around the device so that none of the device edge was exposed to the receptor solution. The device covered with epidermis was attached to the flat side of the Teflon holder of a release rod using nylon netting and nickel wire. The rods were reciprocated in a fixed volume of receptor solution (distilled water). The entire receptor solution was changed at each sampling time. The temperature of the receptor solution in the water bath was maintained at 35° C.

Figure 9:
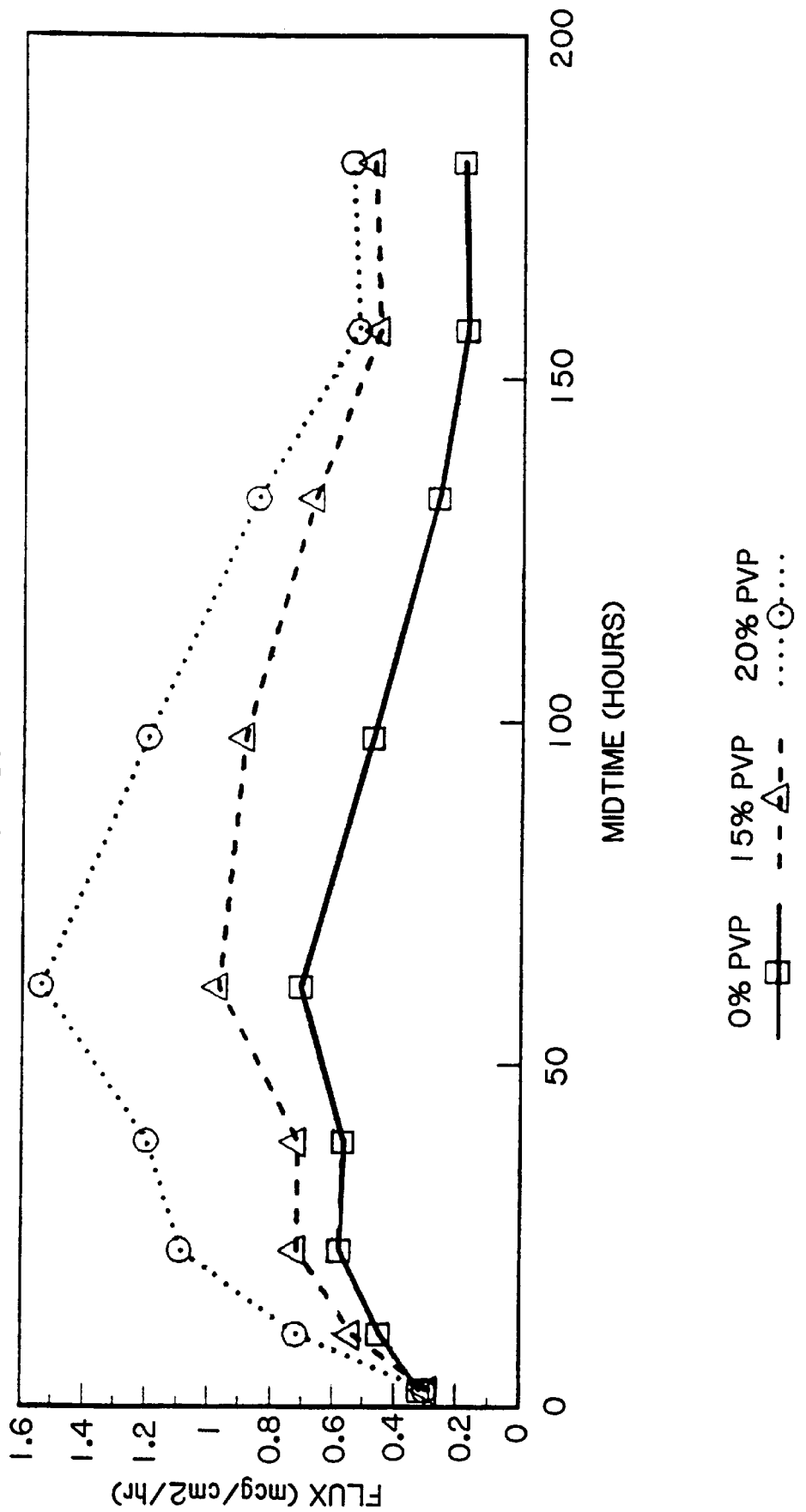
FIG. 9 is a graph showing transdermal flux across cadaver skin at 35° C. of 2.5% gestodene with 0%, 15% and 20% poly-N-vinyl-2-pyrrolidone.

The receptor solutions were stored in capped vials at room temperature until assayed for gestodene content by HPLC. The fluxes achieved for the different systems are shown in FIG. 9. As can be seen from FIG. 9, the drug fluxes for the systems containing N-vinyl-2-pyrrolidone were higher than the drug fluxes for the systems that contained no N-vinyl-2-pyrrolidone.

EXAMPLE 7

The drug/permeation enhancer reservoir was prepared by mixing ethylene vinyl acetate having a vinyl acetate content of 33 percent ("EVA 33", U.S.I. Chemicals, Illinois) and N-vinyl-2-pyrrolidone (Polyplasdone XL-10®, GAF), if present, in an internal mixer (Bra Bender type mixer) until the EVA 33 pellets fused. Gestodene, ethinyl estradiol and glycerol monooleate were then added. The mixture was blended, and calendered to a 4 mil thick film. The compositions of the reservoirs are given in Table 7.

TABLE 7

Drug/Permeation Enhancer Reservoir Composition
(weight percent)

ethinyl estradiol/gestodene/glycerol monooleate/EVA 33
(2/2/20/76)
ethinyl estradiol/gestodene/glycerol monooleate/EVA
33/N-vinyl-2-pyrrolidone
(2/2/20/71/5)

This film was then laminated to an acrylic contact adhesive with a release liner (80912, 3M) on one side and a nylon reinforced polyurethane backing NRU-100-c® (code 80931) (Flexcon Co.) on the opposite side. A ⅝" diameter disc was punched from each film. The films were then observed.

In the composition without the N-vinyl-2-pyrrolidone, there was residue on the release liner. In the composition with the N-vinyl-2-pyrrolidone, there was no residue was on the release liner.

EXAMPLE 8

The drug/permeation enhancer reservoir was prepared by mixing ethylene vinyl acetate having a vinyl acetate content of 33 percent ("EVA 33", U.S.I. Chemicals, Illinois) and N-vinyl-2-pyrrolidone (Polyplasdone XL-10®, GAF), if present, in an internal mixer (Bra Bender type mixer) until the EVA 33 pellets fused. Gestodene, ethinyl estradiol and glycerol monooleate were then added. The mixture was blended, and calendered to a 4 mil thick film. The compositions of the reservoirs are given in Table 8.

TABLE 8

Drug/Permeation Enhancer Reservoir Composition
(weight percent)

ethinyl estradiol/gestodene/glycerol monooleate/EVA 33
(2/2.5/19.3/76.2)
ethinyl estradiol/gestodene/glycerol monooleate/EVA
33/N-vinyl-2-pyrrolidone (2/2.5/19.3/61.2/15)
ethinyl estradiol/gestodene/glycerol monooleate/EVA
33/N-vinyl-2-pyrrolidone (2/2.5/19.3/51.2/25)

This film was then laminated to a nylon reinforced polyurethane backing NRU-100-c® (80931) (Flexcon Co.), such that on one side was a backing and on the other side was a release liner. A ⅝" diameter disc was punched from each film. The films were then observed.

The composition without the N-vinyl-2-pyrrolidone had residue on the release liner and the reservoir surface was matted and oily. In the compositions with the N-vinyl-2-pyrrolidone, no residue was on the release liner and the reservoir surface was smooth with no oily texture.

EXAMPLE 9

The drug/permeation enhancer reservoir was prepared by mixing ethylene vinyl acetate having a vinyl acetate content of 28 percent ("EVA 28", U.S.I. Chemicals, Illinois) and N-vinyl-2-pyrrolidone (Polyplasdone XL-10®, GAF), if present, in an internal mixer (Bra Bender type mixer) until the EVA 28 pellets fused. Gestodene, ethinyl estradiol and glycerol monooleate were then added. The mixture was blended, and calendered to a 4 mil thick film between two release liners. The compositions of the reservoirs are given in Table 9.

TABLE 9

Drug/Permeation Enhancer Reservoir Composition
(weight percent)

ethinyl estradiol/gestodene/glycerol monooleate/EVA 28
(2/5/27.9/65.1)
ethinyl estradiol/gestodene/glycerol monooleate/EVA
33/N-vinyl-2-pyrrolidone
(2/5/27.9/45.1/20)

A ⅝" diameter disc was punched from each film. The films were then observed. The composition without the N-vinyl-2-pyrrolidone had a lot of residue on both release liners. The compositions with the N-vinyl-2-pyrrolidone had residue on cut edges of one release liner.

EXAMPLE 10

The drug/permeation enhancer reservoir was prepared by mixing ethylene vinyl acetate having a vinyl acetate content of 28 percent ("EVA 28", U.S.I. Chemicals, Illinois) and N-vinyl-2-pyrrolidone (Polyplasdone XL-10®, GAF), if present, in an internal mixer (Bra Bender type mixer) until the EVA 28 pellets fused. Glycerol monooleate was then added. The mixture was blended, and calendered to a 4 mil thick film. The compositions of the reservoirs are given in Table 10.

TABLE 10

Drug/Permeation Enhancer Reservoir Composition
(weight percent)

glycerol monooleate/EVA 28
(20/80)
glycerol monooleate/EVA 33/N-vinyl-2-pyrrolidone
(20/75/5)

This film was then laminated to an acrylate contact adhesive (80912, 3M) on one side and a nylon reinforced polyurethane backing NRU-100-c® (code 80931) (Flexcon Co.) on the opposite side. In the composition that did not contain N-vinyl-2-pyrrolidone, the reservoir had glycerol monooleate blooming out and the reservoir surface was oily. The layers did not laminate together at room temperature, nor at a warm setting of a hot plate. When the setting was increased, the layers laminated together. The composition that contained N-vinyl-2-pyrrolidone the layers laminated at room temperature and at an elevated temperature. No leaking of glycerol monooleate was observed.

EXAMPLES 11–12

The drug/permeation enhancer reservoirs were prepared by mixing ethylene vinyl acetate having a vinyl acetate content of 28% ("EVA 28", U.S.I. Chemicals, Illinois) or EVA 40 in the case of the control, and N-vinyl-2-pyrrolidone (Polyplasdone XL®-10, GAF), if present, in an internal mixer (Bra Bender type mixer) until the EVA 28 or 40 pellets fused. Gestodene, ethinyl estradiol and glycerol monooleate were then added. The mixture was blended for approximately 20 minutes at 54–56° C. and 30 rpm. After blending, the mixture was quickly cooled to 40–45° C. and calendered to a 4 mil thick film. The compositions of the reservoirs are given in Table 11.

TABLE 11

Drug/Permeation Enhancer Reservoir Composition
(weight percent)

Ethinyl estradiol/gestodene/glycerol monooleate/EVA 40
(2/2.5/30/35.5)
Ethinyl estradiol/gestodene/glycol monooleate/EVA 40/N-
vinyl-2-pyrrolidone
(2/2.5/30/15.5/20)

The films were then laminated to an acrylate contact adhesive (80912, 3M) on one side and a nylon reinforced polyurethane backing NRU-100-c® (code 80931) (Flexcon Co.) on the opposite side. The films were then cut into circles and taped to prevent edge release.

For each device tested, the adhesive was placed against the stratum corneum side of a disc of human epidermis that had been blotted dry just prior to use. The excess epidermis was then wrapped around the device. The device covered with epidermis was attached to the flat side of the teflon holder of a release rod using nylon netting and nickel wire. The rods were reciprocated in a fixed volume of receptor solution. The entire receptor solution was changed at each sampling time. The temperature of the receptor solution in the water bath was maintained at 35° C.

Figure 10:
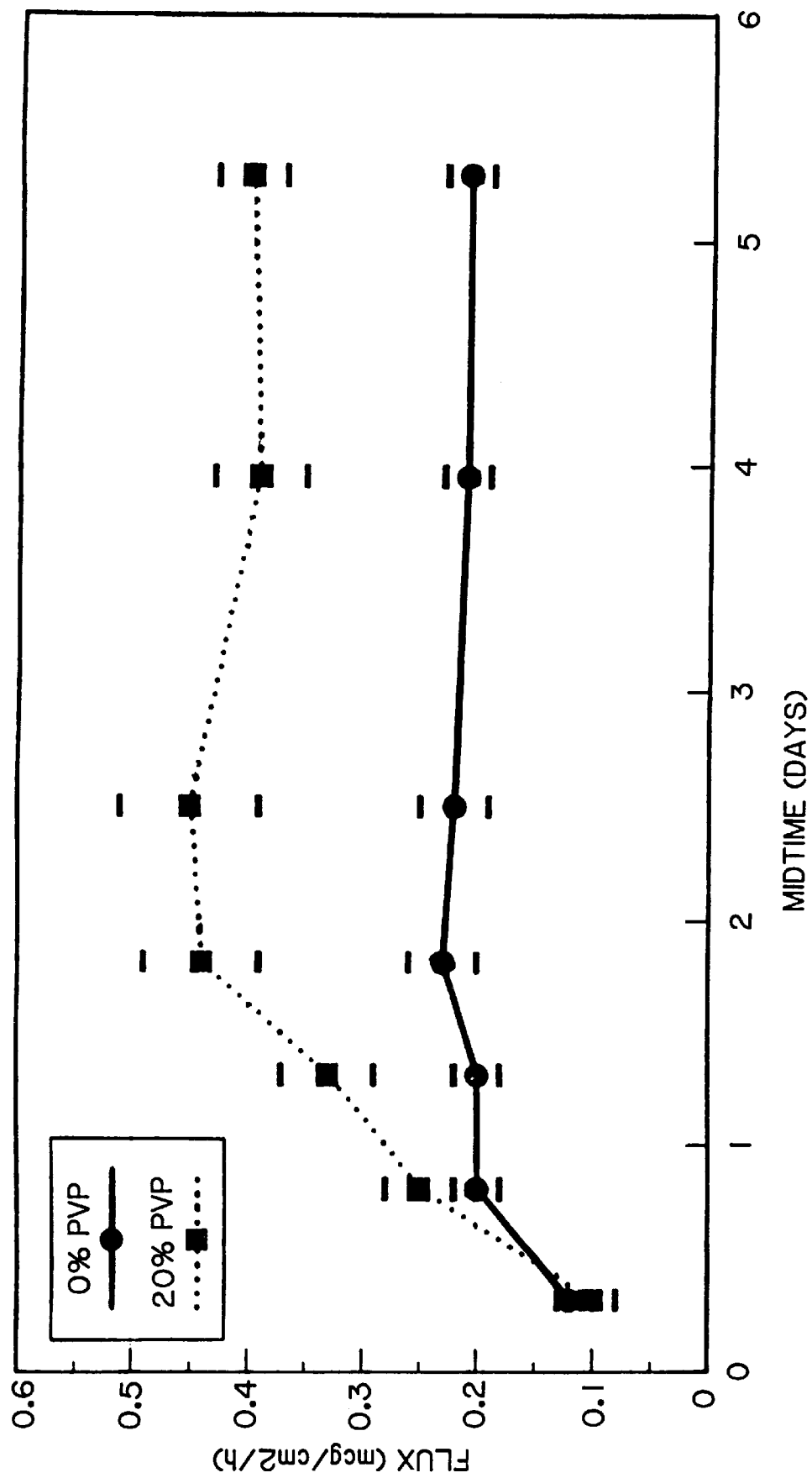
FIG. 10 is a graph showing transdermal flux of gestodene across cadaver skin at 35° C. of 2.5% gestodene and 2% ethinyl estradiol with 0% and 20% poly-N-vinyl-2-pyrrolidone.
Figure 11:
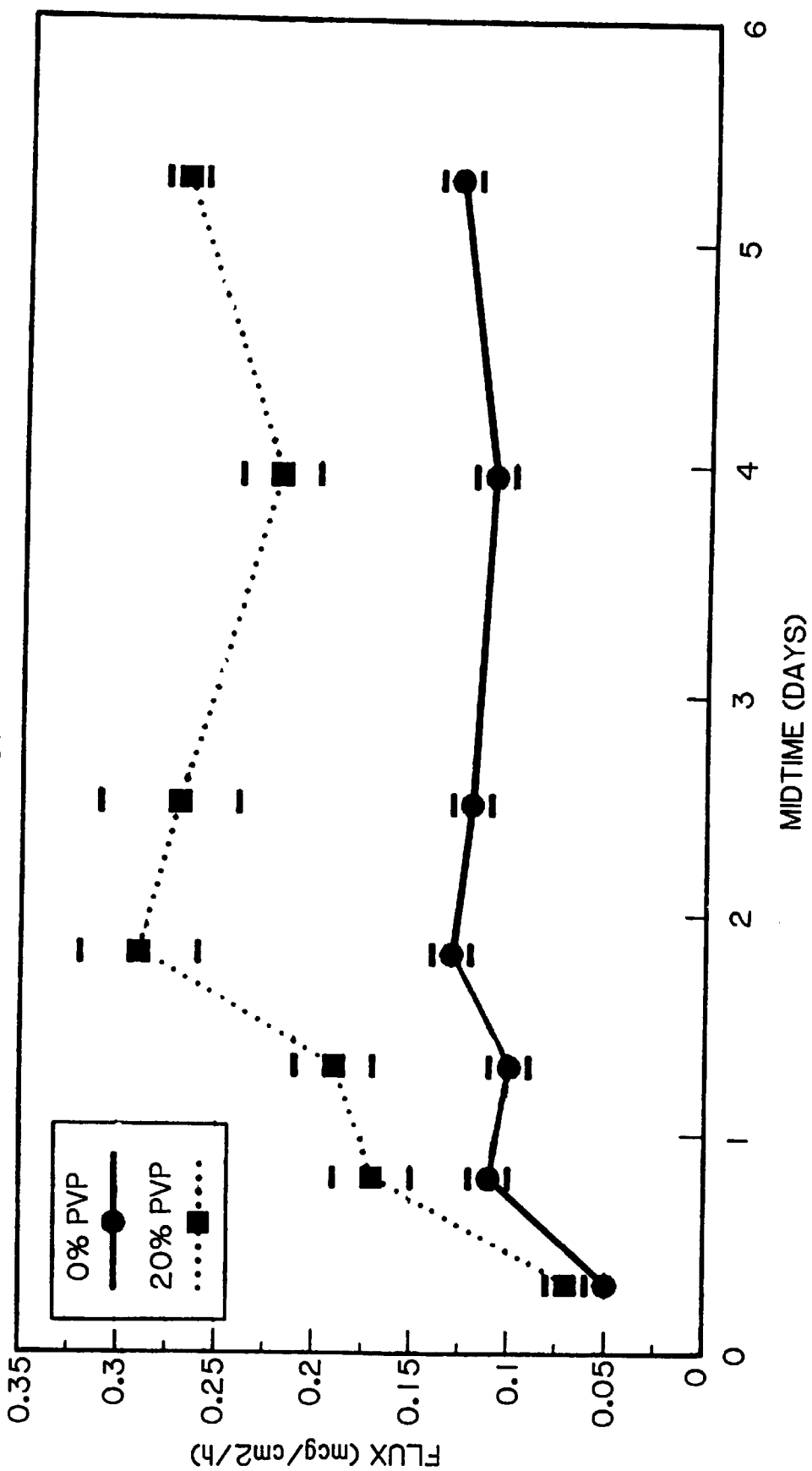
FIG. 11 is a graph showing transdermal flux of ethinyl estradiol across cadaver skin at 35° C. of 2% ethinyl estradiol with 0% and 20% poly-N-vinyl-2-pyrrolidone.
Figure 12:
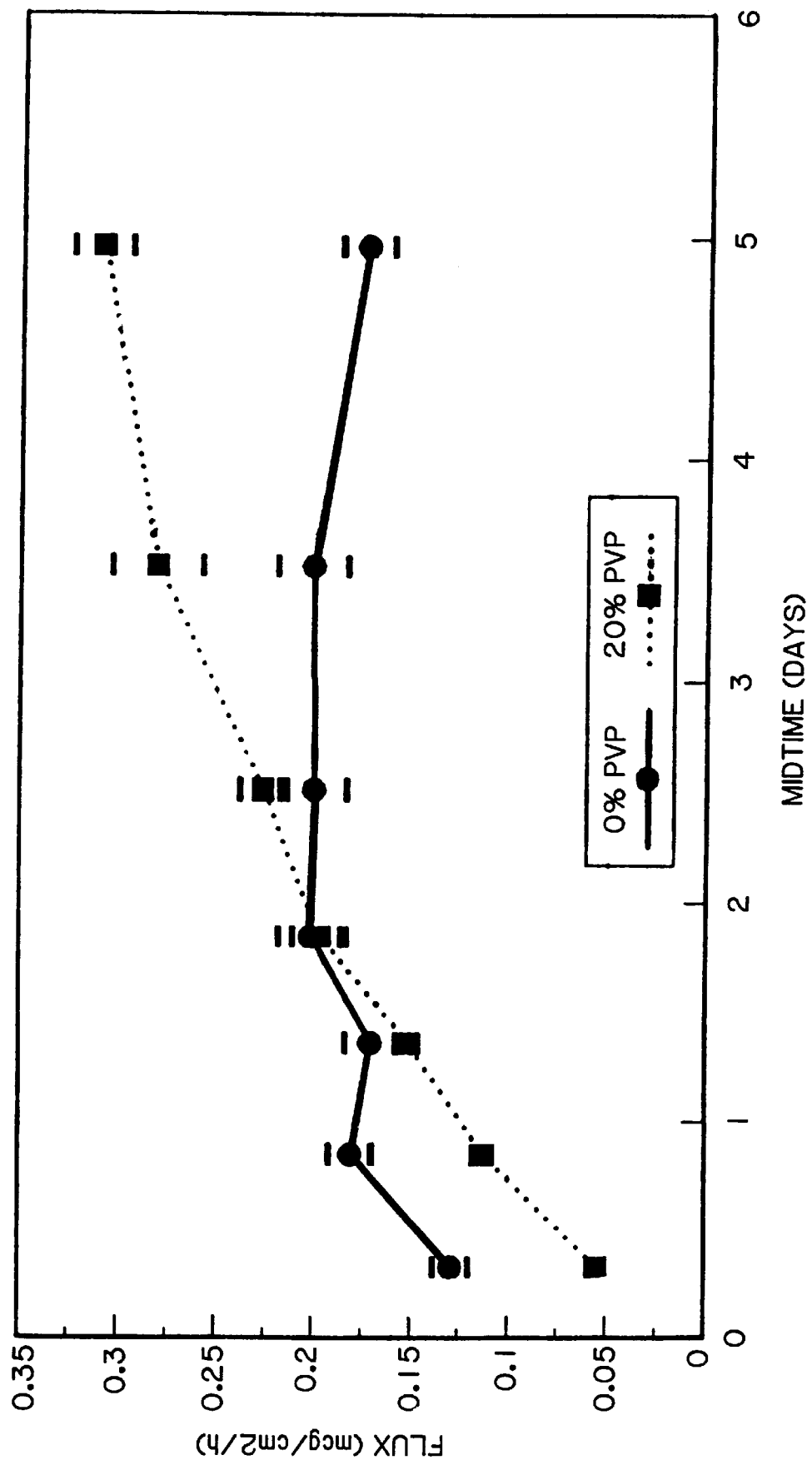
FIG. 12 is a graph showing transdermal flux of gestodene across cadaver skin at 35° C. of 2.5% gestodene and 2% ethinyl estradiol with 0% and 20% poly-N-vinyl-2-pyrrolidone.

The receptor solutions were stored in capped vials at room temperature until assayed for gestodene and ethinyl estradiol content. The fluxes achieved for the different systems and examples are shown in FIGS. 10–13, the gestodene fluxes are shown in FIGS. 10 and 12 and the ethinyl estradiol fluxes are shown in FIGS. 11 and 13. As can be seen from FIGS. 10–13 the drug fluxes for the systems containing N-vinyl-2-pyrrolidone were higher than the drug fluxes for the systems containing no N-vinyl-2-pyrrolidone.

A grand summary showing the effect of N-vinyl-2-pyrrolidone on gestodene transdermal flux of systems made according to the above description containing 30% by weight glycerol monooleate, 2.5% by weight gestodene, 2.0% by weight ethinyl estradiol, and 0 or 20% by weight N-vinyl-2-pyrrolidone in an EVA matrix is shown in FIG. 14.

EXAMPLE 13

The drug/permeation enhancer reservoir was prepared by mixing ethylene vinyl acetate having a vinyl acetate content of 33 percent ("EVA 33", U.S.I. Chemicals, Illinois) and N-vinyl-2-pyrrolidone (Polyplasdone XL® and XL-10®, GAF), if present, in an internal mixer (Bra Bender type mixer) until the EVA 33 pellets fused. Gestodene, ethinyl estradiol and glycerol monooleate were then added. The mixture was blended and calendered to a 4 mil thick film. The compositions of the reservoirs are given in Table 12.

TABLE 12

Drug/Permeation Enhancer Reservoir Composition
(weight percent)

EVA 40/glycerol monooleate/melatonin
(64/30/6)
ethinyl estradiol/gestodene monooleate/
EVA 33/n-vinyl-2-pyrrolidone
(2.0/2.5/25/70.5/0)
ethinyl estradiol/gestodene/glycerol monooleate/
EVA 33/N-vinyl-2-pyrrolidone
(2.0/2.5/0/75.5/20)
ethinyl estradiol/gestodene/glycerol monooleate/
EVA 33/N-vinyl-2-pyrrolidone
(2.0/2.5/0/95.5/0)
ethinyl estradiol/gestodene/glycerol monooleate/
EVA 33/N-vinyl-2-pyrrolidone
(2.0/2.5/30/45.5/20)
ethinyl estradiol/gestodene/glycerol monooleate/
EVA 33/N-vinyl-2-pyrrolidone
(2.0/2.5/30/45.5/20)

The films were then laminated to an acrylate contact adhesive (80912, 3M) on one side and a nylon reinforced polyurethane backing NRU-100-c® (code 80931) (Flexcon Co.) on the opposite side. The films were then cut into circles and taped to prevent edge release. The reservoir compositions were tested on two different skins.

For each device tested, the adhesive was placed against the stratum cornea side of a disc of human epidermis that had been blotted dry just prior to use. The excess epidermis was then wrapped around the device. The device covered with epidermis was attached to the flat side of the Teflon holder of a release rod using nylon netting and nickel wire. The rods were reciprocated in a fixed volume of receptor solution. The entire receptor solution changed at each sampling time. The temperature of the receptor solution in the water bath was maintained at 35° C.

The receptor solutions were stored in capped vials at room temperature until assayed for gestodene content by HPLC. The fluxes achieved for the different systems are shown in FIGS. 15 and 16. As can be seen from FIGS. 15 and 16, the drug fluxes for the systems containing both N-vinyl-2-pyrrolidone and permeation enhancer, glycerol monooleate, were higher than the drug fluxes for the systems containing only permeation enhancer or only N-vinyl-2-pyrrolidone, thus indicating that the combination of permeation enhancer with a n-poly-vinyl amide produces more than an additive effect.

EXAMPLE 14

The laminate reservoir was prepared by mixing ethylene vinyl acetate having a vinyl acetate content at 33 percent ("EVA 33", U.S.I. Chemicals, Illinois) and N-vinyl-2-pyrrolidone (Polyplasdone XL-10®, GAF), if present, in an internal mixer (Bra Bender type mixer) until the EVA 40 pellets fused. Glycerol monooleate was then added. The mixture was blended and calendered to a 4 mil thick film. The compositions of the reservoirs are given in Table 13.

TABLE 13

| Laminate Reservoir Composition (weight percent) |
| --- |
| EVA 33/glycerol monooleate/N-vinyl-2-pyrrolidone (50/30/20) |
| EVA 40/glycerol monooleate (70/30) |

The films were then laminated to an acrylate contact adhesive (80912, 3M) on one side and a nylon reinforced polyurethane backing NRU-100-c® (code 80931) (Flexcon Co.) on the opposite side. A $^{13}\!/_{16}$" diameter disc was punched from each film and the laminates were used in a seven day wear study. Table 14 depicts the results of the wear study.

TABLE 14

| Days Worn | 0% PVPXL-10 | 20% PVPXL-10 |
| --- | --- | --- |
| 0–1 | | |
| 1–2 | | |
| 2–3 | | |
| 3–4 | | |
| 4–5 | 4 | 4 |
| 5–6 | 5, 5 | |
| 6–7 | | |
| removed | 28 | 42 |
| total days worn[1] | 42 | 46 |
| # fall off 0–7 days[2] | 3 | 1 |

[2]The maximum number of possible days worn is 49.
[3]The maximum number of possible fall offs is 7.

As Table 14 indicates, the addition of N-vinyl-2-pyrrolidone into the drug reservoir improves the wearability of a system.

EXAMPLE 15

The laminate reservoir was prepared by mixing ethylene vinyl acetate having a vinyl acetate content of 40 percent ("EVA 40", U.S.I. Chemicals, Illinois) and N-vinyl-2-pyrrolidone (Polyplasdone XL-10®, GAF), if present, or Cabosil (Cabot), if present, in an internal mixer (Bra Bender type mixer) until the EVA 40 pellets fused. Glycerol monolaurate and lauryl lactate were then added. The mixture was blended and calendered to a 4 mil thick film. The compositions of the reservoirs are given in Table 15.

TABLE 15

| Backing | Laminate Reservoir Composition (weight percent) | Inline Adhesive |
| --- | --- | --- |
| Sontara | EVA 40/GML/(60/25/15) | 3M |
| Sontara | EVA 40/GML/LL/CaboSil(55/25/15/5) | 3M |
| Sontara | EVA 40/GML/LL/CaboSil(50/25/15/10) | 3M |
| Sontara | EVA 40/GML/LL/N-vinyl-2-pyrrolidone(50/25/15/10) | 3M |
| Sontara | EVA 40/GML/LL/N-vinyl-2-pyrrolidone(40/25/15/20) | 3M |

The films were then laminated to an acrylate content adhesive with a release liner on one side (80912, 3M) and a Sontara (80632B CN 352790) backing on the opposite side.

Table 16 depicts the summary of wearing times for this example. As Table 16 indicates the total days worn for the systems containing N-vinyl-2-pyrrolidone is greater than for those containing no N-vinyl-2-pyrrolidone.

TABLE 16

| | Summary of Wearing Times | | | | |
| --- | --- | --- | --- | --- | --- |
| Days Worn | No Additive | 5% Cabosil | 10% Cabosil | 10% PVPXL-10 | 20% PVPXL-10 |
| 0–1 | .6* .9* | .5 .4* .9* | .4* .9* | .9* | |
| 1–2 | | 1.8 | 1.5 | | |
| 2–3 | | | | | 2.9* |
| 3–4 | | | 3.0 | 3.0 | |
| 4–5 | | 4.5 | | | 4.9* |
| 5–6 | 5.0 | | | | 5.8* |
| 6–7 | | | | 6.1 | |
| removed[1] | 77.0 | 63.0 | 70.0 | 84.0 | 77.0 |
| total days worn[2] | 83.5 | 71.1 | 75.8 | 91.0 | 90.6 |
| # fall offs 0–3 days[3] | 2 | 4 | 3 | 1 | 1 |
| # fall offs 0–7 days[3] | 3 | 5 | 4 | 2 | 3 |

*indicates systems that fell while exercising or while bathing
[1]The value is equal to the number of individuals in which the system was removed times seven days.
[2]The maximum number of possible days worn is 98.
[3]The maximum number of possible tall offs is 14.

EXAMPLE 16

The laminate reservoir was prepared by mixing ethylene vinyl acetate having a vinyl acetate content of 40 percent ("EVA 40", U.S.I. Chemicals, Illinois) and N-vinyl-2-pyrrolidone (Polyplasdone XL-10®, GAF), if present, in an internal mixer (Bra Bender type mixer) until the EVA 40 pellets fused. Glycerol monolaurate and lauryl lactate were then added. The mixture was blended and calendered to a 4.0 mil thick film. The films were then laminated to an acrylate contact adhesive with a release liner on one side (80912, 3M) and either a medpar or cloth backing Sontara (80632B Cn 352790) or on the opposite side. The compositions of the reservoirs are given in Table 17.

TABLE 17

| Backing | Reservoir Formulation (weight percent) |
| --- | --- |
| Cloth | EVA 40/GML/LL(60/25/15) |
| Cloth | EVA 40/GML/LL/N-vinyl-2-pyrrolidone(50/25/15/10) |

TABLE 17-continued

| Backing | Reservoir Formulation (weight percent) |
|---------|----------------------------------------|
| Cloth   | EVA 40/GML/LL/N-vinyl-2-pyrrolidone(40/25/15/20) |
| Medpar  | EVA 40/GML/LL(60/25/15) |
| Medpar  | EVA 40/GML/LL/N-vinyl-2-pyrrolidone(50/25/15/10) |
| Medpar  | EVA 40/GML/LL/N-vinyl-2-pyrrolidone(40/25/15/20) |

The systems were then used in a seven day wear study.

The results of the wear study are depicted in Table 18 and FIGS. 15 and 16.

TABLE 18

Systems Remaining on at Time Given

| Days worn | Cloth 0% PVP | Cloth 10% PVP | Cloth 20% PVP | MEDPAR 0% PVP | MEDPAR 10% PVP | MEDPAR 20% PVP |
|-----------|--------------|---------------|---------------|----------------|-----------------|-----------------|
| 0 days    | 12 | 13 | 13 | 13 | 13 | 13 |
| 0–1 days  | 8  | 12 | 13 | 2  | 4  | 5  |
| 1–2 days  | 7  | 12 | 12 | 1  | 1  | 3  |
| 2–3 days  | 7  | 12 | 12 | 0  | 1  | 3  |
| 3–4 days  | 6  | 12 | 11 | 0  | 1  | 3  |
| 4–5 days  | 5  | 10 | 10 | 0  | 1  | 2  |
| 5–6 days  | 4  | 9  | 9  | 0  | 1  | 1  |
| 6–7 days  | 2  | 8  | 9  | 0  | 1  | 1  |
| 7–8 days  | 2  | 8  | 9  | 0  | 1  | 0  |
| removed   | 2  | 8  | 9  | 0  | 1  | 0  |

As is seen in FIGS. 15 and 16, and in Table 18, the systems containing N-vinyl-2-pyrrolidone displayed a higher patch survival rate, ie, the patches stayed on the subject longer than those without the N-vinyl-2-pyrrolidone.

While the invention has been described with reference to specific embodiments, it will be apparent to those skilled in the art that many alternatives, modifications and variations may be needed. Accordingly, it is intended to embrace all such alternatives, modifications, and variations that may fall within the spirit and scope at the appended claims.

What is claimed is:

1. A device for the transdermal administration of a drug at a therapeutically effective rate comprising:
   (a) a reservoir comprising:
      (i) 1–40 wt % of a transdermally administerable drug;
      (ii) 30–70 wt % of a polymeric matrix comprising ethylene vinyl acetate copolymer having 9–60% vinyl acetate content;
      (iii) 10–40 wt % of a monoglyceride or a mixture of monoglycerides of a fatty acid with a total monoesters content of at least 51% or a lactic ester of an alcohol, separately or in combination; and
      (iv) 5–25 wt % poly-N-vinyl-2-pyrrolidone;
   (b) a backing adjacent the skin-distal surface of the device; and
   (c) means for maintaining the reservoir in drug- and permeation enhancer-transmitting relation with the skin.

2. A device according to claim 1 wherein the drug is selected from the group consisting of buspirone, melatonin, tacrine, testosterone, alprazolam, estradiol and gestodene.

3. A device according to claim 2 wherein the permeation enhancer is selected from the group consisting of glycerol monolaurate, glycerol monooleate, glycerol monolinoleate, or lauryl lactate, separately or in combination.

4. A device for the transdermal administration of a drug at a therapeutically effective rate comprising:
   (a) a first reservoir comprising:
      (i) 1–40 wt % of a transdermally administerable drug;
      (ii) 30–70 wt % of a polymeric matrix comprising ethylene vinyl acetate copolymer having 9–60% vinyl acetate content;
      (iii) a permeation enhancer comprising 10–40 wt % of a monoglyceride or a mixture of monoglycerides of a fatty acid with a total monoesters content of at least 51% or a lactic ester of an alcohol, separately or in combination; and
      (iv) 5–25 wt % poly-N-vinyl-2-pyrrolidone;
   (b) a second reservoir comprising said permeation enhancer, poly-N-vinyl-2-pyrrolidone, and optionally, said drug;
   (c) a rate-controlling membrane between the first and second reservoirs;
   (d) a backing adjacent the skin-distal surface of the device; and
   (e) means for maintaining the reservoir in drug- and permeation enhancer-transmitting relation with the skin.

5. A device according to claim 4 wherein the drug is selected from the group consisting of buspirone, melatonin, tacrine, testosterone, alprazolam, estradiol, and gestodene.

6. A device according to claim 5 wherein the permeation enhancer is selected from the group consisting of glycerol monolaurate, glycerol monooleate, glycerol monolinoleate, or lauryl lactate, separately or in combination.

7. A method for increasing the transdermal flux of a drug from a transdermal device comprising:
   (a) incorporating into a reservoir of a transdermal device 5–25 wt % poly-N-vinyl-2-pyrrolidone, wherein said device comprises:
      (i) a reservoir comprising a transdermally administerable drug and 10–40 wt % of a monoglyceride or a mixture of monoglycerides of a fatty acid with a total monoesters content of at least 51% or a lactic ester of an alcohol, separately or in combination;
      (ii) a backing layer adjacent the skin distal surface of the device;
      (iii) means for maintaining the reservoir in drug and permeation enhancer transmitting relation with the skin; and
   (b) placing the device onto the skin of a person.

8. A method for improving adhesion of a transdermal device comprising:
  (a) incorporating into a reservoir of a transdermal device 5–25 wt % poly-N-vinyl-2-pyrrolidone, wherein said device comprises:
    (i) a reservoir comprising a transdermally administerable drug and 10–40 wt % of a monoglyceride or a mixture of monoglycerides of a fatty acid with a total monoesters content of at least 51% or a lactic ester of an alcohol, separately or in combination;
    (ii) a backing layer adjacent the skin distal surface of the device;
    (iii) means for maintaining the reservoir in drug and permeation enhancer transmitting relation with the skin; and
  (b) placing the device onto the skin of a person.

9. A method for increasing the stability of a transdermal device comprising:
  (a) incorporating into a reservoir of a transdermal device 5–25 wt % poly-N-vinyl-2-pyrrolidone, wherein said device comprises:
    (i) a reservoir comprising a transdermally administerable drug and 10–40 wt % of a monoglyceride or a mixture of monoglycerides of a fatty acid with a total monoesters content of at least 51% or a lactic ester of an alcohol, separately or in combination;
    (ii) a backing layer adjacent the skin distal surface of the device; and
    (iii) means for maintaining the reservoir in drug and permeation enhancer transmitting relation with the skin.

* * * * *